United States Patent
Power et al.

(10) Patent No.: US 12,138,382 B2
(45) Date of Patent: Nov. 12, 2024

(54) VACCINE ADMINISTRATION APPARATUS AND METHOD

(71) Applicant: Stamford Devices Limited, Galway (IE)

(72) Inventors: John Power, Galway (IE); Ronan MacLoughlin, Craughwell (IE); Michael Casey, Galway (IE); Conor Duffy, County Galway (IE); Aidan Duffy, Knocknacarra (IE)

(73) Assignee: Stamford Devices Limited, Galway (IE)

( * ) Notice: Subject to any disclaimer, the term of this patent is extended or adjusted under 35 U.S.C. 154(b) by 679 days.

(21) Appl. No.: 17/371,412

(22) Filed: Jul. 9, 2021

(65) Prior Publication Data

US 2022/0016365 A1  Jan. 20, 2022

(30) Foreign Application Priority Data

Jul. 14, 2020 (EP) .................................... 20185705
Jan. 29, 2021 (EP) .................................... 21154205

(51) Int. Cl.
*A61M 11/04* (2006.01)
*A61M 11/00* (2006.01)
(Continued)

(52) U.S. Cl.
CPC ........... *A61M 11/04* (2013.01); *A61M 11/003* (2014.02); *A61M 15/0065* (2013.01);
(Continued)

(58) Field of Classification Search
CPC ................ A61M 11/04; A61M 11/003; A61M 15/0065; A61M 15/0085; A61M 15/0086;
(Continued)

(56) References Cited

U.S. PATENT DOCUMENTS 4,949,526 A * 8/1990 Brogna .................... G07F 13/10
   221/268
4,953,545 A * 9/1990 McCarty ........... A61M 15/0086
   128/200.14
(Continued)

FOREIGN PATENT DOCUMENTS

CN    111179504 A    5/2020
EP    1 743 671 A1   1/2007
(Continued)

OTHER PUBLICATIONS

International Search Report and Written Opinion mailed Oct. 19, 2021 in International Application No. PCT/EP2021/069140 (17 pages).
(Continued)

*Primary Examiner* — Nicolas A Arnett
(74) *Attorney, Agent, or Firm* — Bookoff McAndrews, PLLC

(57) ABSTRACT

A dispensing apparatus is for use by users to take a chamber, fill the chamber with an aerosolized vaccine or other medicament, and dispose of used chambers. A display provides instructions to encourage prompt inhalation by the user from a dispensed and filled chamber. The apparatus allows very fast administration of vaccines to large numbers of people. The aerosol dispenser apparatus detects the chamber is in correct position and delivers a pre-determined dose of aerosol. Once the dose is delivered a visual and/or audible indicator informs the user that the chamber is filled and that they can take the inhalation. The single dose aerosol chamber is optimized for efficient administration of an aerosol.

32 Claims, 20 Drawing Sheets

(51) Int. Cl.
*A61M 15/00* (2006.01)
*B67D 7/02* (2010.01)
*G07F 7/06* (2006.01)
*G07F 13/02* (2006.01)
*G07F 17/00* (2006.01)
*G16H 20/13* (2018.01)
*G16H 40/63* (2018.01)

(52) U.S. Cl.
CPC .... *A61M 15/0085* (2013.01); *A61M 15/0086* (2013.01); *A61M 15/009* (2013.01); *B67D 7/0283* (2013.01); *G07F 7/0609* (2013.01); *G07F 13/025* (2013.01); *G07F 17/0092* (2013.01); *G16H 20/13* (2018.01); *G16H 40/63* (2018.01); *A61M 2202/30* (2013.01); *A61M 2205/0205* (2013.01); *A61M 2205/0238* (2013.01); *A61M 2205/10* (2013.01); *A61M 2205/502* (2013.01); *A61M 2205/581* (2013.01); *A61M 2205/583* (2013.01); *A61M 2206/12* (2013.01); *A61M 2209/045* (2013.01); *A61M 2210/0618* (2013.01); *A61M 2210/0625* (2013.01)

(58) Field of Classification Search
CPC ............ A61M 15/009; A61M 2202/30; A61M 2205/0205; A61M 2205/0238; A61M 2205/10; A61M 2205/502; A61M 2205/581; A61M 2205/583; A61M 2205/12; A61M 2209/045; A61M 2210/0618; A61M 2210/0625; B67D 7/0283; G07F 7/0609; G07F 13/025; G07F 17/0092; G16H 20/13; G16H 40/63
See application file for complete search history.

(56) References Cited

U.S. PATENT DOCUMENTS

| | | | | |
|---|---|---|---|---|
| 6,513,524 | B1 * | 2/2003 | Storz | A61M 16/208 128/203.29 |
| 6,571,790 | B1 * | 6/2003 | Weinstein | A61J 1/00 128/200.14 |
| 6,782,886 | B2 * | 8/2004 | Narayan | A61M 11/005 128/200.14 |
| 8,945,605 | B2 * | 2/2015 | Boucher | A61M 11/003 424/434 |
| 9,682,202 | B2 * | 6/2017 | Wachtel | A61M 15/0021 |
| 9,984,213 | B2 * | 5/2018 | Howieson | A61J 1/03 |
| 10,589,040 | B1 * | 3/2020 | Hyde | A61M 15/0021 |
| 11,305,073 | B2 * | 4/2022 | Stenzler | A61M 15/0085 |
| 2009/0076650 | A1 * | 3/2009 | Faes | G07F 11/42 700/231 |
| 2010/0096399 | A1 * | 4/2010 | Ratnakar | A61J 7/0418 434/262 |
| 2010/0230435 | A1 * | 9/2010 | Wegelin | G07F 13/025 340/5.82 |
| 2013/0197693 | A1 * | 8/2013 | Kamen | G06Q 50/22 700/244 |
| 2014/0291414 | A1 * | 10/2014 | Bretillot | B05B 17/0615 239/102.2 |
| 2016/0001019 | A1 * | 1/2016 | Fink | A61M 11/005 128/200.14 |
| 2016/0331913 | A1 * | 11/2016 | Bourque | A61M 15/0043 |
| 2018/0133417 | A1 * | 5/2018 | Krishna | A61M 15/0021 |
| 2022/0016360 | A1 * | 1/2022 | Power | A61M 15/009 |

FOREIGN PATENT DOCUMENTS

| | | | |
|---|---|---|---|
| EP | 1474196 B1 * | 8/2016 | ............ A61J 1/065 |
| EP | 3 141 275 A1 | 3/2017 | |
| EP | 3 583 968 A1 | 12/2019 | |
| WO | 97/07896 A1 | 3/1997 | |
| WO | 02/17988 | 3/2002 | |
| WO | 2005/102431 A2 | 11/2005 | |
| WO | 2010/008424 | 1/2010 | |
| WO | 2012046220 A1 | 4/2012 | |
| WO | 2013/107992 A1 | 7/2013 | |
| WO | 2013186031 A3 | 12/2013 | |
| WO | 2015010809 A1 | 1/2015 | |
| WO | 2016/024099 A1 | 2/2016 | |
| WO | 2016198667 A1 | 12/2016 | |
| WO | 2017055166 A1 | 4/2017 | |
| WO | 2018/069675 A1 | 4/2018 | |
| WO | 2019/094628 A1 | 5/2019 | |
| WO | 2019/136437 A1 | 7/2019 | |

OTHER PUBLICATIONS

International Search Report and Written Opinion mailed Dec. 14, 2021 in International Application No. PCT/EP2021/069137 (22 pages).

Partial International Search Report mailed Oct. 22, 2021 in International Application No. PCT/EP2021/069137 (8 pages).

* cited by examiner

VACCINE ADMINISTRATION APPARATUS AND METHOD

CROSS-REFERENCE TO RELATED APPLICATIONS

This patent application claims the benefit of priority to European Patent Application No. EP20185705.9, filed on Jul. 14, 2020 and European Patent Application No. EP21154205.5, filed Jan. 29, 2021, the entireties of which are incorporated herein by reference.

INTRODUCTION

The invention relates to administration of aerosol to people, whether therapeutic or non-therapeutic. It applies especially to administration of aerosols where the exact volume is not critical, but where it is sufficient that a base volume is reliably administered, such as vaccines.

It is known to deliver an aerosol dose into a chamber, such as described in U.S. Pat. No. 10,589,040. This has an inhaler opening, an inner barrier, and a one-way inhalation valve. U.S. Pat. No. 4,953,545 describes a disposable chamber for an inhaler.

The present invention is directed towards providing for administration of aerosol doses such as vaccines to large numbers of people in a fast, effective, and cost-efficient manner.

SUMMARY OF THE INVENTION

We describe an aerosol dispensing apparatus comprising a controller, a dispenser with a support for a single dose aerosol chamber having a nebulizer delivery port and an inhalation port, and a nebulizer having an aerosol generator and an outlet conduit adapted to deliver an aerosol dose into the chamber via the nebulizer delivery port. Preferably, the dispenser is configured for automatic engagement of the nebulizer outlet conduit with the nebulizer delivery port and for separation after delivery of a dose.

Preferably, the dispenser comprises an automated chamber handler for engagement of chambers with the nebulizer in an automated manner. Preferably, the nebulizer is configured to deliver doses according to a pre-set time at a pre-set flow rate. Preferably, the apparatus further comprises a chamber dispenser for dispensing chambers to users in proximity to the nebulizer.

Preferably, the apparatus further comprises a user interface with a display screen and/or a speaker, and the controller is configured to generate user instructions for use of the apparatus and for inhalation from the chamber. Preferably, the controller is configured to instruct user inhalation from a chamber within a set period of time. Preferably, the controller is configured to provide instructions to consume the aerosol within 10 seconds. Preferably, the controller is configured to generate an advisory communication via the interface concerning a desired number of inhalations and breaths. Preferably, the controller is configured to generate an advisory communication advising a maximum of two breaths. Preferably, the controller is configured to generate an advisory communication to advise a user to have a short inhalation.

Preferably, the apparatus further comprises a receptacle for used chambers. Preferably, the apparatus is arranged in a series of stages including a stage for (a) dispensing a chamber, (b) for filling a chamber, and (c) for disposing of used chambers.

Preferably, the nebulizer is configured to deliver doses of between 0.05 mL and 0.25 mL. Preferably, the nebulizer is configured to deliver at a flow rate in excess of 0.01 mL/min. Preferably, the nebulizer is configured to deliver at a flow rate in the range of 0.5 mL/min to 2.5 mL/min. Preferably, the nebulizer is configured for delivery of aerosol into a chamber in less than 15 seconds.

Preferably, the dispenser comprises an automated chamber handler for engagement of chambers with the nebulizer in an automated manner, and said handler comprises a chamber holder which is movable from a chamber receiving position to an aerosol generator engagement position.

Preferably, the receiver comprises a sensor to detect presence of a chamber in the receiver, and the controller is configured to trigger a filling cycle upon detection of a chamber in the receiver, and preferably the receiver is annular.

Preferably, the sensor is configured to detect concentricity of a chamber in the receiver. Preferably, the receiver is on an arm which is rotatable from a chamber-receiving user-facing front position to a filling rear position. Preferably, the arm supports a dispensing stage cover at an end opposed from the receiver, such that the cover is presented to a user during filling to provide an interlock. Preferably, the cover is curved to present a convex surface towards a front of the dispensing station.

Optionally, the nebulizer comprises a support which supports the aerosol generator during movement from an inoperative position to an operative position for filling. Preferably, the inoperative position is above the chamber in use.

Preferably, the support is movable on a vertical rail to move the aerosol generator between said positions. Preferably, the nebulizer comprises a chamber sensor to detect presence of a chamber in engagement with the outlet conduit, and the controller is configured to commence aerosolization only upon said detection of a chamber. Optionally, the nebulizer comprises a pusher to push against the chamber during disengagement of the outlet conduit to prevent movement of the chamber or a lid of the chamber Preferably, the nebulizer comprises a vibratory mesh aperture plate, a vibration drive for causing vibration of the aperture plate, and a reservoir for delivering a treatment liquid to a top surface of the aperture plate, such that vibration of the aperture plate causes aerosol to enter the outlet conduit. Optionally, the aperture plate apertures are sized to provide aerosol droplets, at least 80% of which have a size less than 6 µm, and also optionally the aperture plate has apertures with a size in the range of 0.5 µm to 10 µm, preferably 0.5 µm to 6.0 µm. Preferably, the aperture plate has in excess of 100 aerosol-forming apertures per square mm. Preferably, the aperture plate has an upper reservoir layer with liquid supply cavities and a lower layer of aerosol-forming apertures. Preferably, the reservoir layer liquid supply cavities have a diameter in the range of 20 µm to 400 µm.

Preferably, the nebulizer is configured to automatically detect end of dose on the aperture plate and to stop operation of the nebulizer if there is no liquid on the aperture plate and provide an alert at the interface accordingly. Optionally, the controller is configured to perform steps of: measuring aperture plate drive current at each of a plurality of measuring points in a scan, each measuring point having a drive frequency; determining a minimum value of the drive current in said scan; determining a value for maximum rate of change of drive current during the scan; and using the minimum value in combination with said maximum rate of change value to execute an algorithm to calculate an indicator value for end-of-dose. Optionally, the controller is configured to utilize a ratio of a maximum slope value and a minimum parameter value to provide said indicator, and preferably the controller is configured to multiply a ratio or a value derived from the ratio by a constant value to provide the indicator. Preferably, the controller is configured to perform the scan across a frequency range of 128 kHz to 165 kHz, and optionally the controller initiates the scan in response to a trigger of possible end of dose.

Preferably, the nebulizer is configured to supply only a single dose to the aerosol generator for each dispensing operation of filling a chamber.

We also describe a method of providing aerosol for treating a plurality of patients using an apparatus of any example described herein, the method comprising automatically delivering aerosol doses into each of a series of single dose chambers, and automatically providing instructions via the interface to a user for inhalation.

Preferably, the controller provides instructions for inhalation within an advised period of time. Preferably, the method includes automatic engagement of the nebulizer outlet conduit with the chamber nebulizer delivery port and separation of the conduit from the chamber after delivery of a dose. In some examples, the nebulizer delivers an aerosolized vaccine into the chambers.

Preferably, the dispenser comprises an automated chamber handler and said handler performs movement of each chamber and engagement of the chambers with the aerosol generator outlet conduit in an automated manner. Preferably, the nebulizer delivers doses for a pre-set time at a pre-set flow rate.

Optionally, the method further comprises a chamber dispenser dispensing chambers to users in proximity to the nebulizer.

Preferably, the apparatus further comprises a user interface with a display screen and/or a speaker, and the controller generates user instructions via said interface for use of the apparatus and for inhalation from the chamber. Preferably, the controller provides advisory and/or alert user information including a desired number of inhalations and breaths, for example an advisory communication advising a maximum of two breaths. Preferably, the controller generates an advisory communication to advise a user to have a short inhalation.

Optionally, the method further comprises a receptacle receiving used chambers. Preferably, the apparatus delivers doses of between 0.05 mL and 0.25 mL. Preferably, the nebulizer performs delivery in less than 15 seconds. Preferably, the nebulizer aerosolizes with a flow rate in the range of 0.5 mL/min to 2.5 mL/min, more preferably 0.75 mL/min to 1.5 mL/min.

Preferably, the dispenser comprises an automated chamber handler for engagement of chambers with the nebulizer in an automated manner, and said handler comprises a chamber holder which moves from a chamber receiving position to an aerosol generator engagement position.

Preferably, the receiver comprises a sensor to detect presence of a chamber in the receiver, and the controller triggers a filling cycle upon detection of a chamber in the receiver. Preferably, the sensor detects concentricity of a chamber in the receiver. Optionally, the receiver is on an arm which is rotated from a chamber-receiving front position to a filling rear position. Preferably, the arm supports a dispensing stage cover at an end opposed from the receiver, the cover is presented to a user during filling to act as an interlock, and the chamber receiver is presented to the user for placement of a chamber.

Preferably, the nebulizer is moved from an inoperative position to an operative position for filling, and the inoperative position is above the chamber in use. Preferably, the liquid which is aerosolized has a viscosity in the range of 1 to 15 cP and a surface tension in the range of 0.5 mN/m and 72 mN/m.

Preferably, the nebulizer comprises a chamber sensor to detect presence of a chamber in engagement with the outlet conduit, and the controller commences aerosolization only upon said detection of a chamber. Optionally, the nebulizer comprises a pusher which pushes against the chamber during disengagement of the outlet conduit to prevent movement of the chamber or a lid of the chamber Preferably, the nebulizer comprises a vibratory mesh aperture plate, a vibration drive for causing vibration of the aperture plate, and a reservoir for delivering a treatment liquid to a top surface of the aperture plate, such that vibration of the aperture plate causes aerosol to enter the outlet conduit, and the aperture plate provides aerosol droplets at least 80% of which have a size of less than 6 µm.

Preferably, the nebulizer automatically detects end of dose on the aperture plate and stops operation of the aerosol generator if there is no liquid on the aperture plate and provides an alert at the interface accordingly. Preferably, the controller performs steps of: measuring aperture plate drive current at each of a plurality of measuring points in a scan, each measuring point having a drive frequency; determining a minimum value of the drive current in said scan; determining a value for maximum rate of change of drive current during the scan; and using the minimum value in combination with said maximum rate of change value to execute an algorithm to calculate an indicator value for end-of-dose. Preferably, the controller utilizes a ratio of a maximum slope value and a minimum parameter value to provide said indicator.

Preferably, the time from chamber dispensing to inhalation is less than 60 seconds. Preferably, the time for delivery of the aerosol into the chamber is less than 15 seconds. Preferably, the controller provides a user advice that time for inhalation should be less than 10 seconds after completion of delivery of the aerosol.

Preferably, the nebulizer provides only a single dose to the aerosol generator for each chamber filling operation.

We also describe a single dose aerosol chamber for administration of a single dose of an aerosol from a nebulizer, the chamber comprising a container, a nebulizer delivery port configured to engage a nebulizer outlet conduit, and an inhalation port or user inhalation of contents of the container, the container being configured for receiving aerosol via the nebulizer delivery port, and mixing of the aerosol with gas in the container for delivery via the inhalation port.

The top wall may be in the form of a removable lid.

Preferably, the container comprises a base, a top wall, and a sidewall extending between the base and the top. Preferably, the nebulizer delivery port is in the top wall. Preferably, the inhalation port is in the top wall. Preferably, the inhalation port is in a raised portion of the top wall.

Preferably, the inhalation port is oblong, preferably having a long axis in a circumferential direction. Preferably, the nebulizer delivery port is off-centre with respect to an axis of the container, adjacent the side wall.

Preferably, the nebulizer delivery port is in the top wall and adjacent the side wall. Preferably, the inhalation port is adjacent the side wall on a side opposed to the nebulizer delivery port. Preferably, the container is of an insulating material, optionally a polymer and/or a wood-derived material.

Preferably, the container volume is in the range of 100 mL to 600 mL, and for many applications it is preferred that the chamber volume is in the range of 150 mL to 400 mL.

Preferably, the side wall tapers to narrow the container downwardly towards a base. Preferably, the nebulizer delivery port has an area in the range of 30 mm² to 700 mm². For some applications such as delivery to the lungs with a high efficiency the nebulizer delivery port preferably has an area in the range of 30 mm² to 120 mm².

Optionally, the container comprises a viewing window for viewing contents. Optionally, the container comprises a hydrophobic material on an internal surface. Optionally, there are one or more apertures in the base of the container. Optionally, there is an anti-microbial coating on an external surface of the chamber. Optionally, the chamber comprises a valve to prevent escape of aerosol from the container after dispensing. Optionally, the container comprises a plurality of vents to limit pressure build-up during dispensing. Optionally, the inhalation port comprises a nasal interface. Optionally, the inhalation port includes a face mask. Optionally, the inhalation port comprises a mouthpiece. Optionally, the chamber includes a baffle for selective rain-out of aerosol for droplet size filtering. Optionally, the baffle is tubular, extending inwardly from the nebulizer delivery port.

We also describe use of a single dose aerosol chamber of any example for delivery of an aerosol to a user, by delivering aerosol into the container through the nebuliser delivery port and user inhalation of the aerosol through the inhalation port.

Optionally, the time period between delivery of aerosol through the nebulizer coupling port and inhalation is less than 60 seconds. Optionally, the aerosol is delivered through the nebulizer delivery port in less than 15 seconds. Optionally, the aerosol is inhaled through the inhalation port in less than 10 seconds. Optionally, the dose has a volume in the range of 0.5 mL to 0.25 mL.

In some examples, the aerosol is a vaccine, such as a Covid-19 vaccine.

Additional Statements

We describe an aerosol chamber for single dose administration of an aerosol dose, the chamber being disposable and comprising a container, an aerosol inlet configured to engage a nebulizer outlet conduit, and an inhalation port for user inhalation of contents of the container.

Preferably, the aerosol inlet is in a top wall of the chamber. Preferably, the inhalation port is in a top wall of the chamber. Preferably, the inhalation port is in a raised portion of the chamber. Preferably, the inhalation port is oblong, preferably having a long axis in a circumferential direction. Preferably, the aerosol inlet is adjacent a wall of the chamber. Preferably, the aerosol inlet is in a top wall of the chamber and adjacent a side wall of the chamber. Preferably, the inhalation port is adjacent a side wall of the chamber on a side opposed to the aerosol inlet.

Preferably, the container is of an insulating material such as a polymer or a paper-based material. Preferably, the chamber comprises a viewing window for viewing contents. Preferably, the chamber comprises a hydrophobic material on an internal surface. Preferably, the chamber resembles a beverage cup in overall configuration.

In some examples, there are one or a number of apertures in a base of the chamber. In some examples, there is an anti-microbial coating on an external surface of the chamber.

We also describe an aerosol dispensing apparatus comprising a dispensing station with a support for a chamber and a nebulizer adapted to deliver an aerosol dose into the chamber via the aerosol inlet. In some examples, the nebulizer is on an automated support for automatic engagement of a nebulizer outlet conduit with the chamber aerosol inlet and separation after delivery of a dose. In some examples, there is an automated chamber handler for engagement of chambers with the nebulizer in an automated manner.

In some examples, the nebulizer is configured to deliver doses according to a pre-set time at a pre-set flow rate. In some examples, the apparatus further comprises a chamber dispenser for dispensing chambers to users in proximity to the nebulizer.

In some examples, the apparatus further comprises a user interface with a display screen, a speaker, and a controller to generate user instructions for use of the apparatus and for inhalation from the chamber. In some examples, the user interface is configured to instruct user inhalation from a chamber within a set period of time. Preferably, the apparatus further comprises a receptacle for used chambers.

In some examples, the apparatus is arranged in a series of stages including a stage for (a) dispensing a chamber, (b) filling a chamber, and (c) disposing of used chambers. In some examples, the apparatus is configured to deliver doses between 0.05 mL and 0.25 mL. In some examples, the nebulizer is configured for delivery in less than 15 seconds.

In some examples, the apparatus has a user interface configured to advise a maximum number of breaths and/or inhalations, for example it may stipulate a maximum of 2 breaths and/or may also advise a short inhalation.

We also describe a method of treating a plurality of patients using an apparatus of any example, the method comprising automatically delivering doses into a series of chambers and providing instructions to a user to take a chamber and inhale from it within an advised period of time. In some examples, the nebulizer delivers an aerosolized vaccine into the chambers.

DETAILED DESCRIPTION OF THE INVENTION

The invention will be more clearly understood from the following description of some embodiments thereof, given by way of example only with reference to the accompanying drawings in which.

Figure 6:
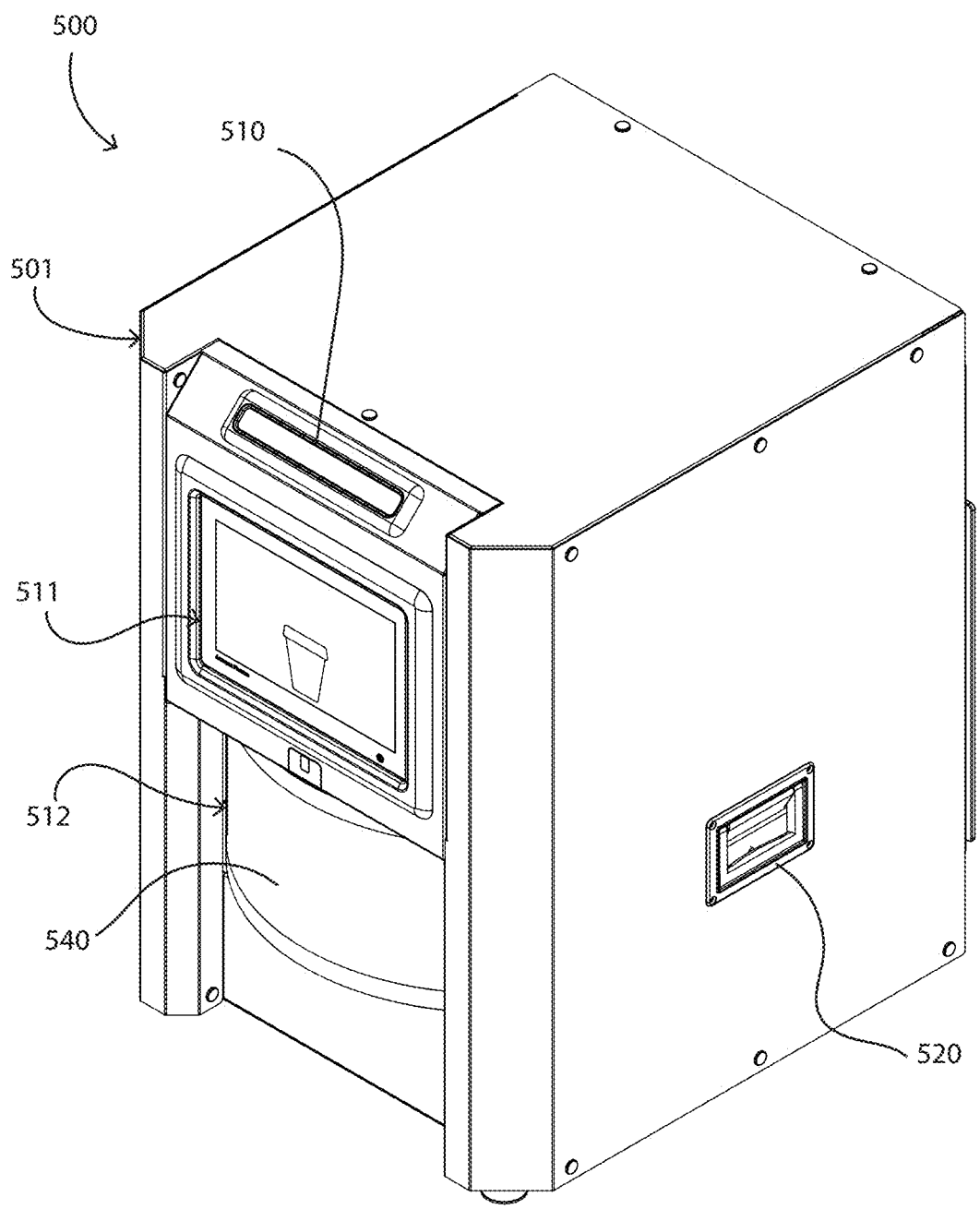
Figure 7:
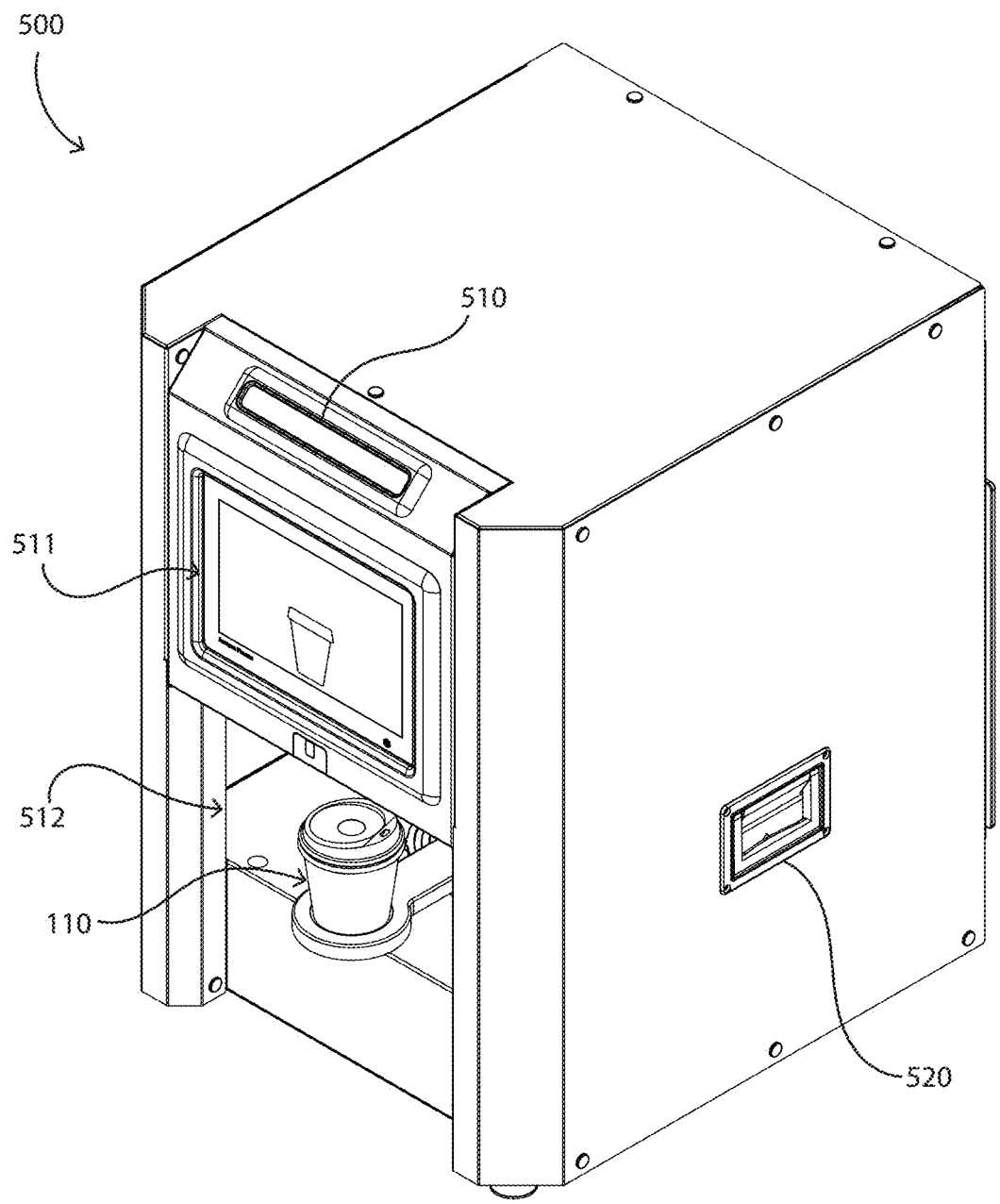
Figure 8:
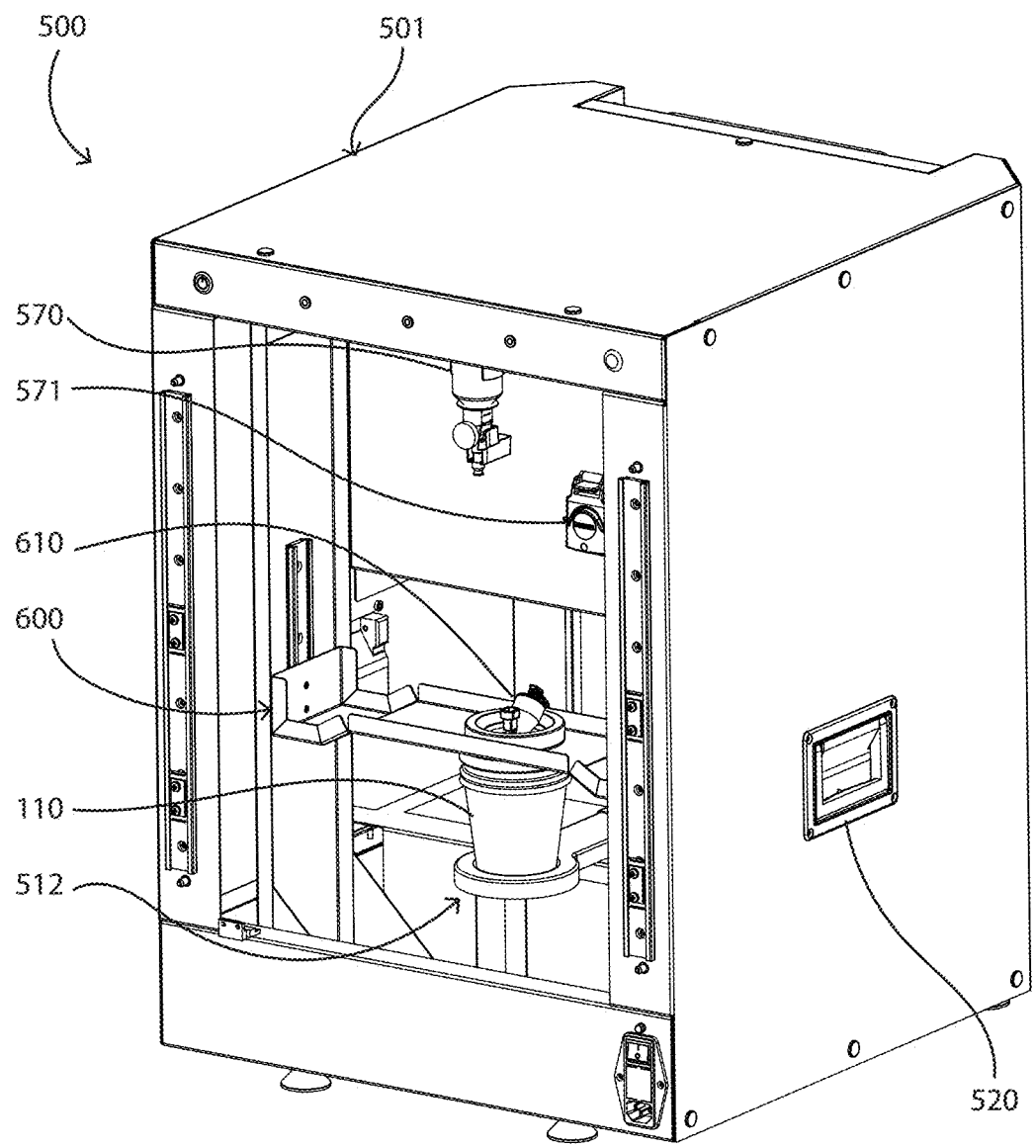
Figure 9:
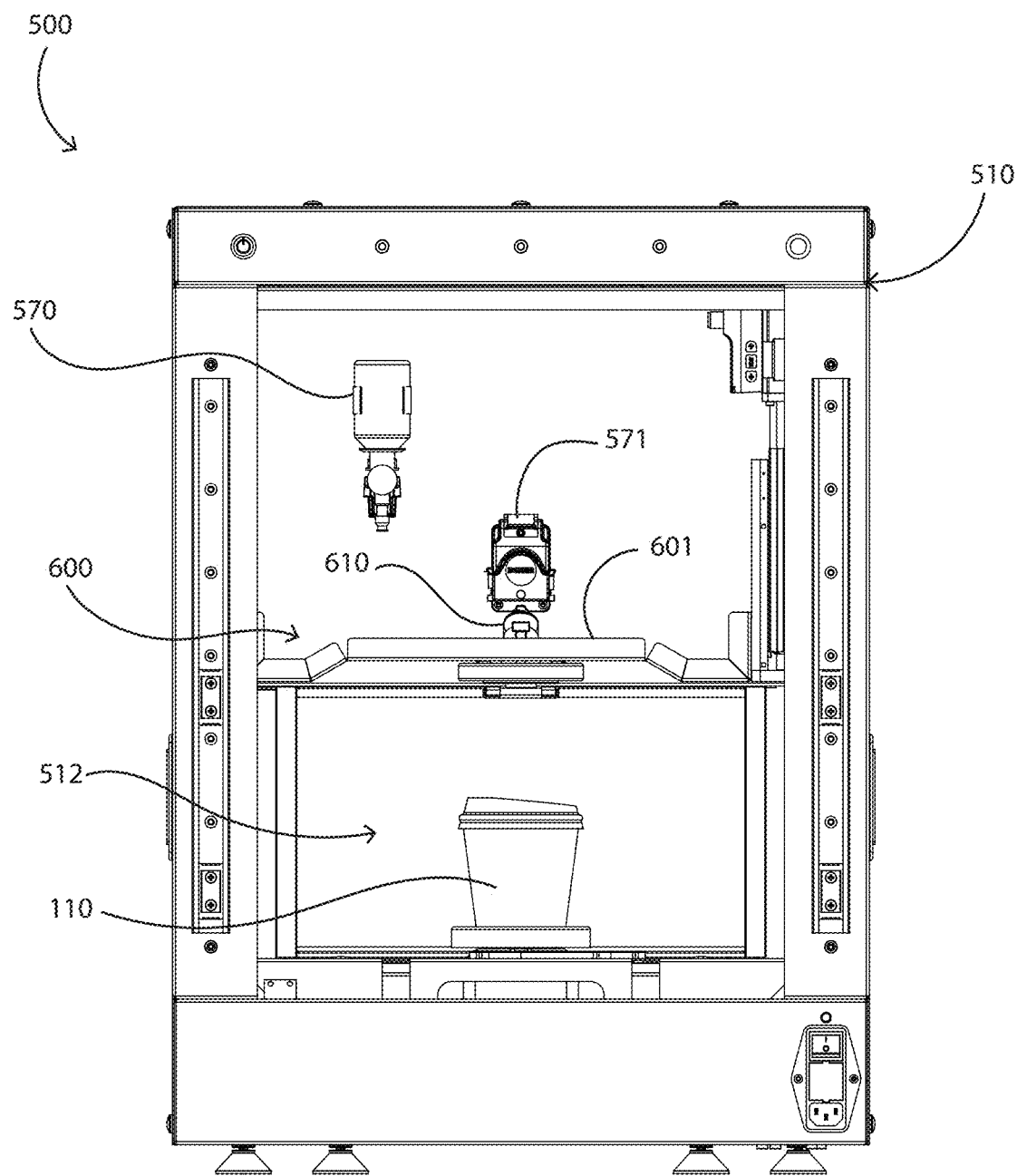
Figure 10:
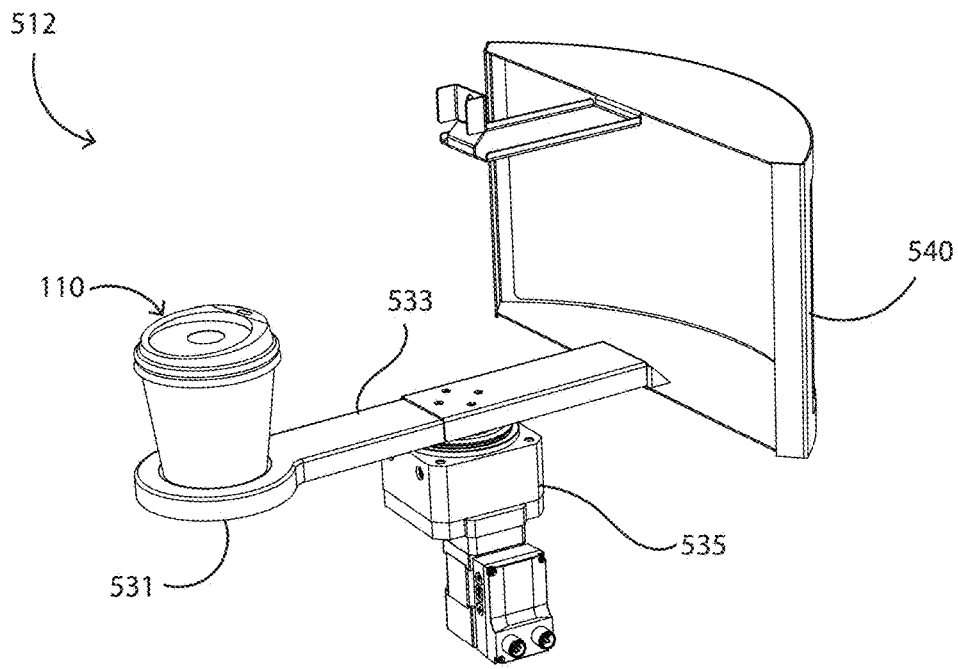
Figure 11:
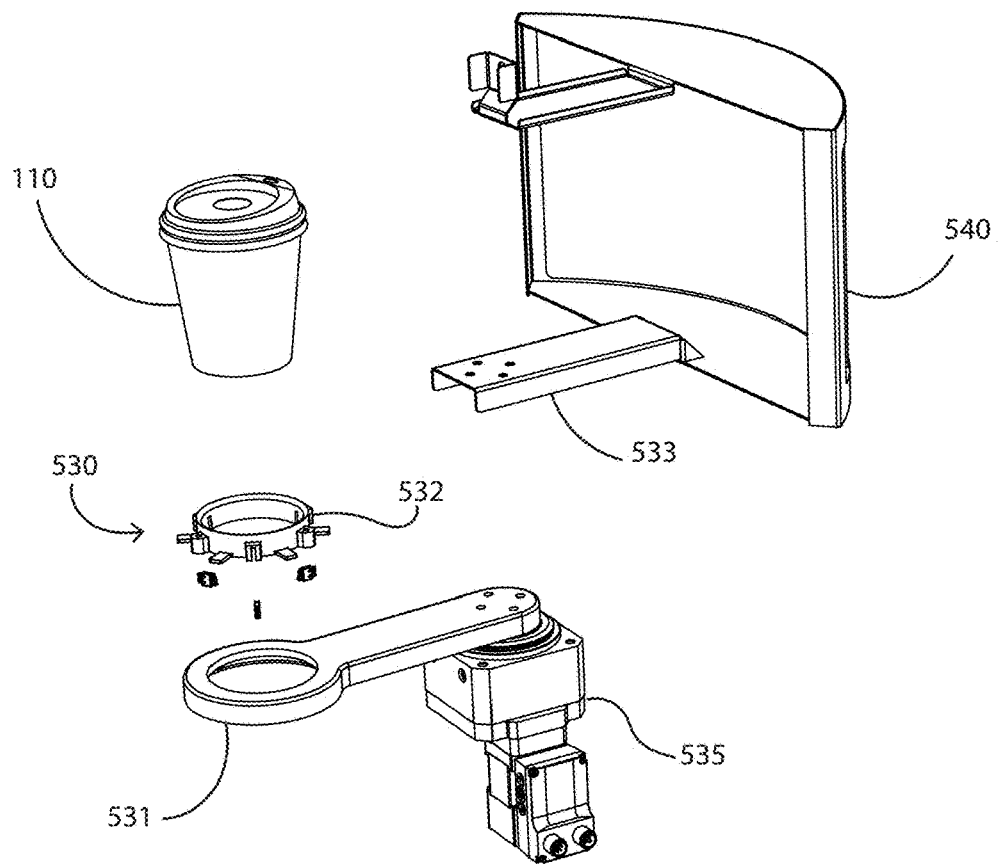
Figure 12:
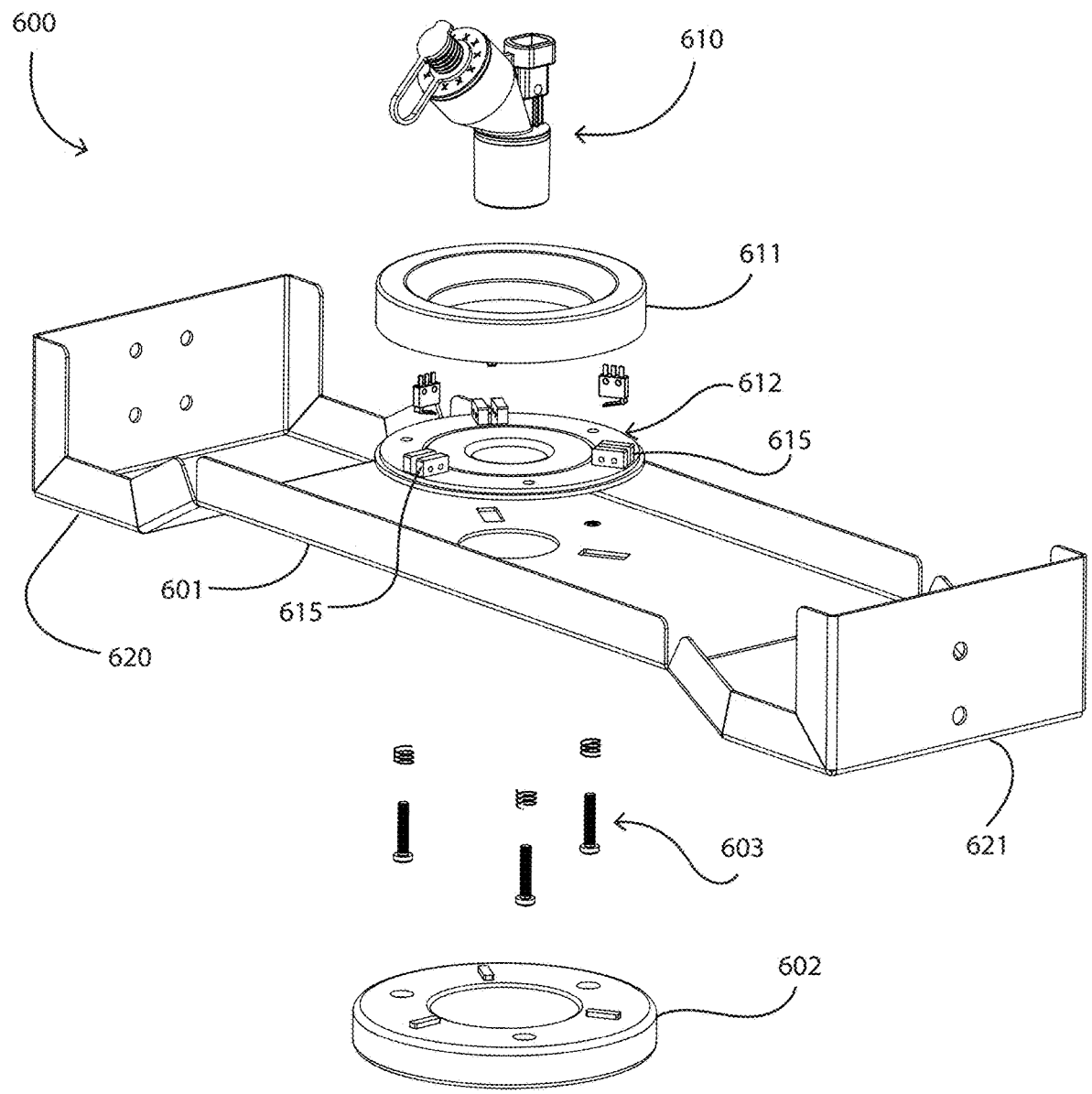
Figure 13:
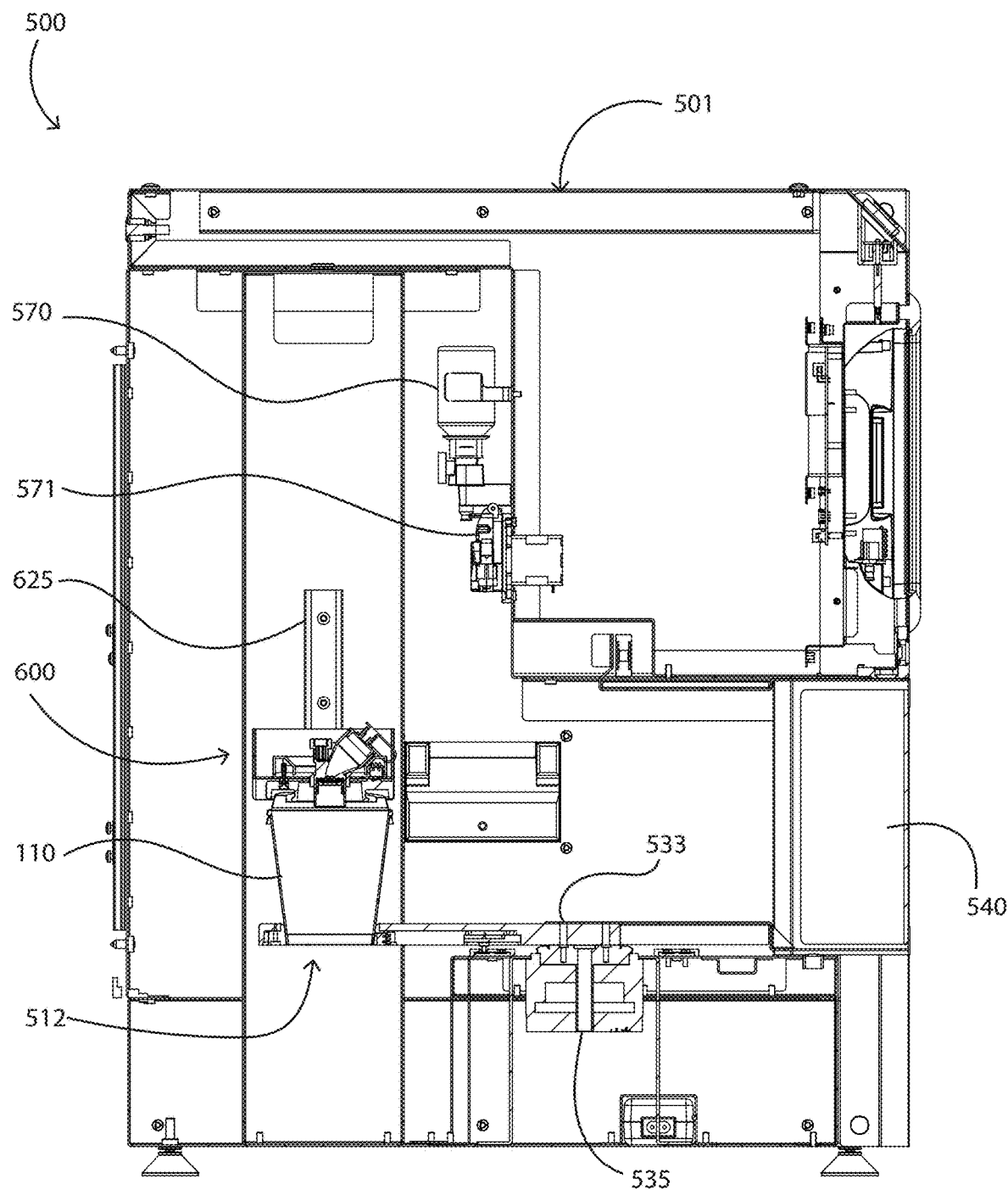
Figure 14:
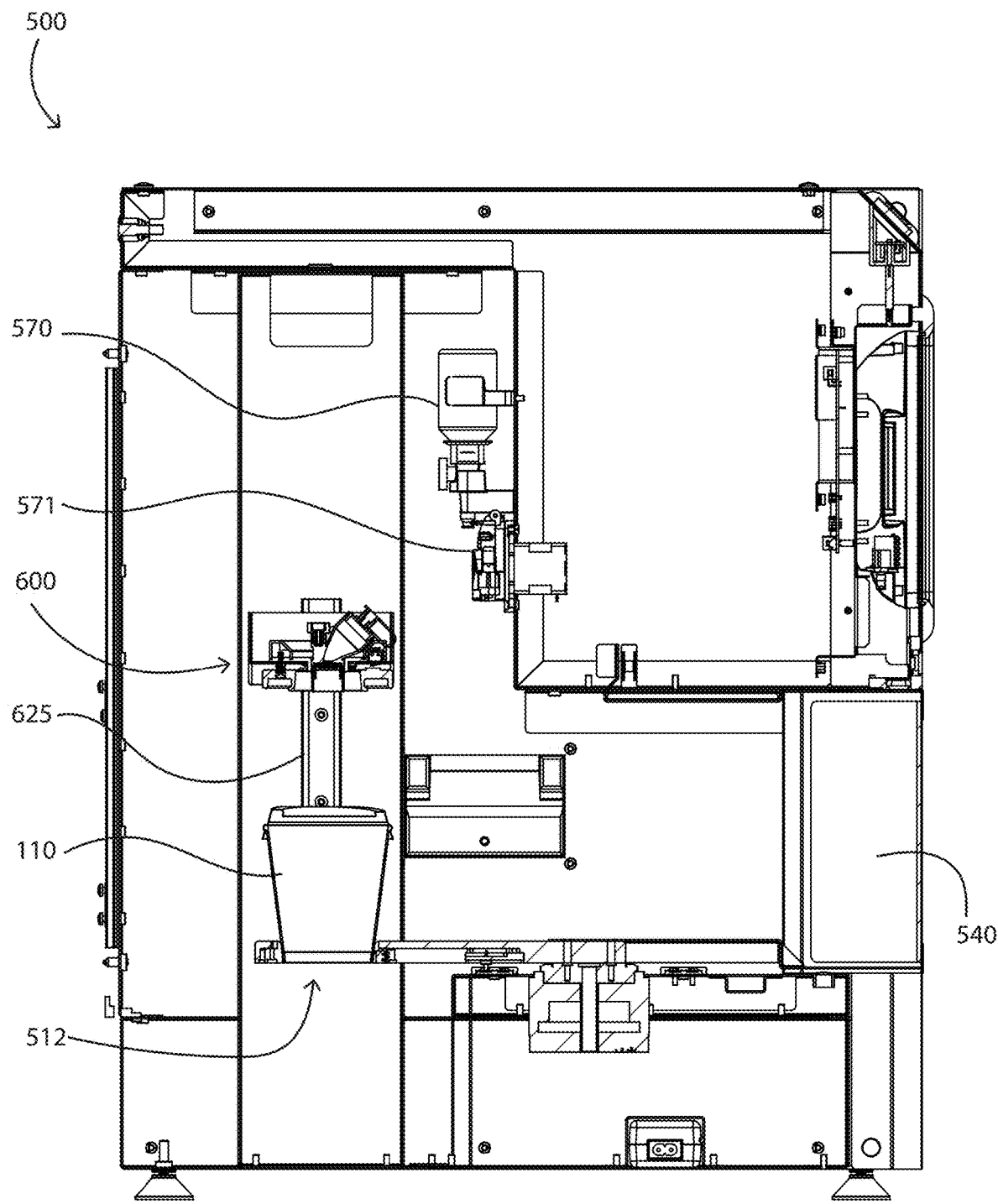
Figure 15:
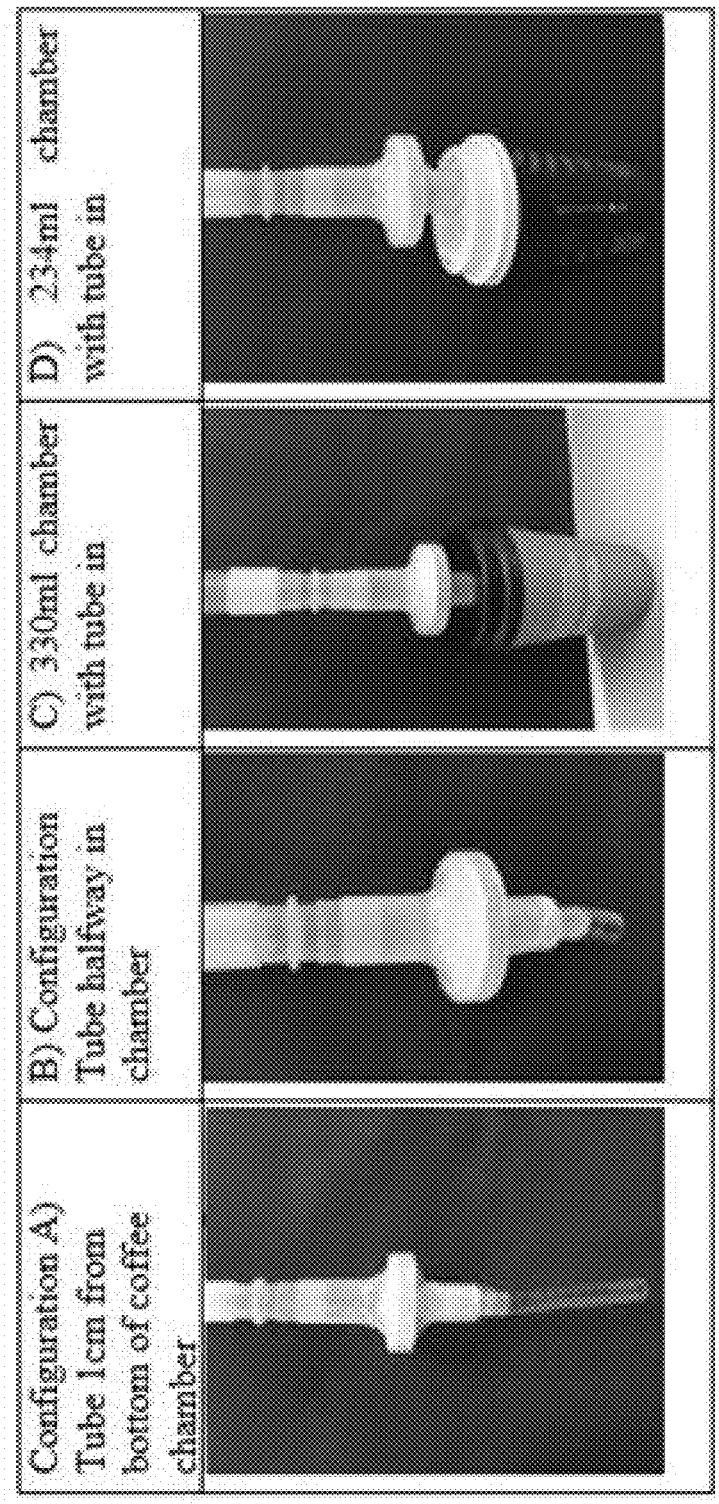

FIGS. 5(a) to (g) inclusive are a series of annotated images illustrating the benefits of mutual locations of the aerosol fill opening and inhalation port of the chamber;

FIGS. 6 to 9 are views of an alternative dispensing apparatus, in this case being smaller, for mounting on a desk or the like, in which FIG. 6 is a perspective view showing the front of the apparatus with an interlock operative, FIG. 7 is a perspective view showing the front when it is presenting a chamber to be taken by a user, and FIGS. 8 and 9 are perspective and elevational views showing the rear of the apparatus with a rear cover removed;

FIG. 10 is a perspective view of an interlocking automated chamber handler of the dispensing apparatus, and FIG. 11 is an exploded view;

FIG. 12 is an exploded view of an automated nebulizer which works in co-ordination with the chamber handler;

FIGS. 13 and 14 are side views showing the automated nebulizer in use; and FIG. 15 is a set of images showing different configurations of use of a filled chamber for test purposes.

A dispensing apparatus or "station" 100 is for use by users to take a single dose device (or "aerosol chamber") 110, fill the chamber with an aerosolized medicament such as a vaccine, and dispose (120) of used chambers 110. A display 103 provides instructions to encourage prompt inhalation by the user from a dispensed and filled chamber. The station allows very fast administration of vaccines or other aerosolized medicaments to large numbers of people. The aerosol dispenser apparatus 100 detects if the chamber is in correct position and delivers a pre-determined dose of aerosol. Once the dose is delivered a visual and/or audible indicator informs the user that the chamber is filled and that they can take the inhalation.

Figure 1:
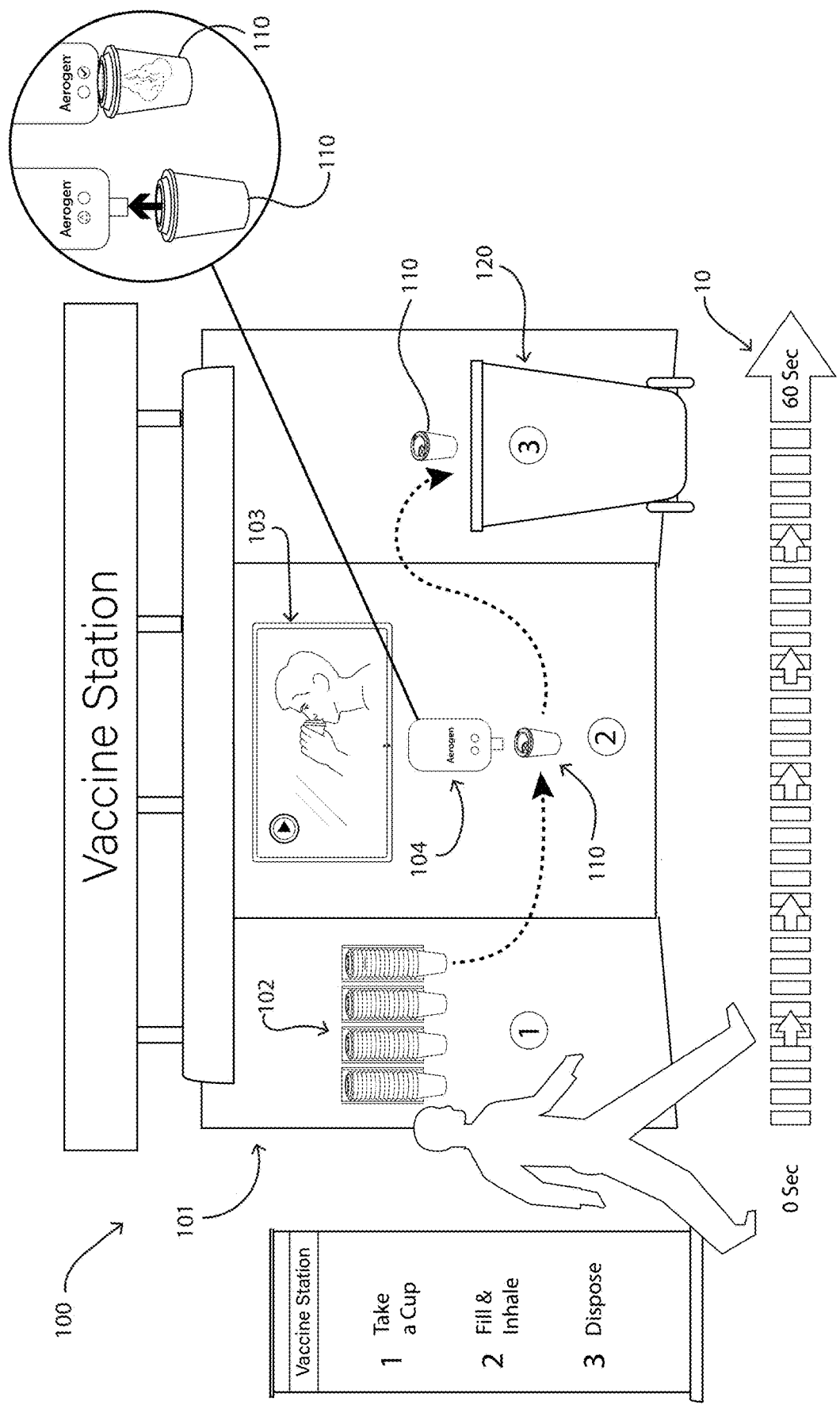
FIG. 1 is a diagram illustrating a vaccine station and its method of use for dispensing a vaccine in a fast manner to a person with minimal requirement for trained staff.

In more detail, referring to FIG. 1 the apparatus 100 has a housing 101 with a first stage 1 for dispensing of disposable single use/dose devices, namely aerosol chambers 110. There is a second stage with an instruction display screen 103 linked with a processor and a memory, and a vaccine dispenser 104 for delivery of a dose of aerosolized vaccine into a chamber 110. A third stage comprises a disposal container 120 for safe disposal of the used chambers 110. As illustrated by the arrow 10 there is a typical timeline of only about 60 seconds for these three stages.

The apparatus 1 has a main controller with digital data processors, for controlling overall operation of the apparatus, including both the generation of user instructions at the interface 103 and also the high-level control instructions for the nebulizer/dispenser 104. The nebulizer 104 has a dedicated controller which controls low-level operation of the nebulizer 104, such as controlling the piezoelectric actuator with a desired frequency (typically 128 kHz) and voltage and time durations.

The dispensing stage comprises a platform upon which the chamber 110 rests during filling.

Aerosol Generator

Figure 2:
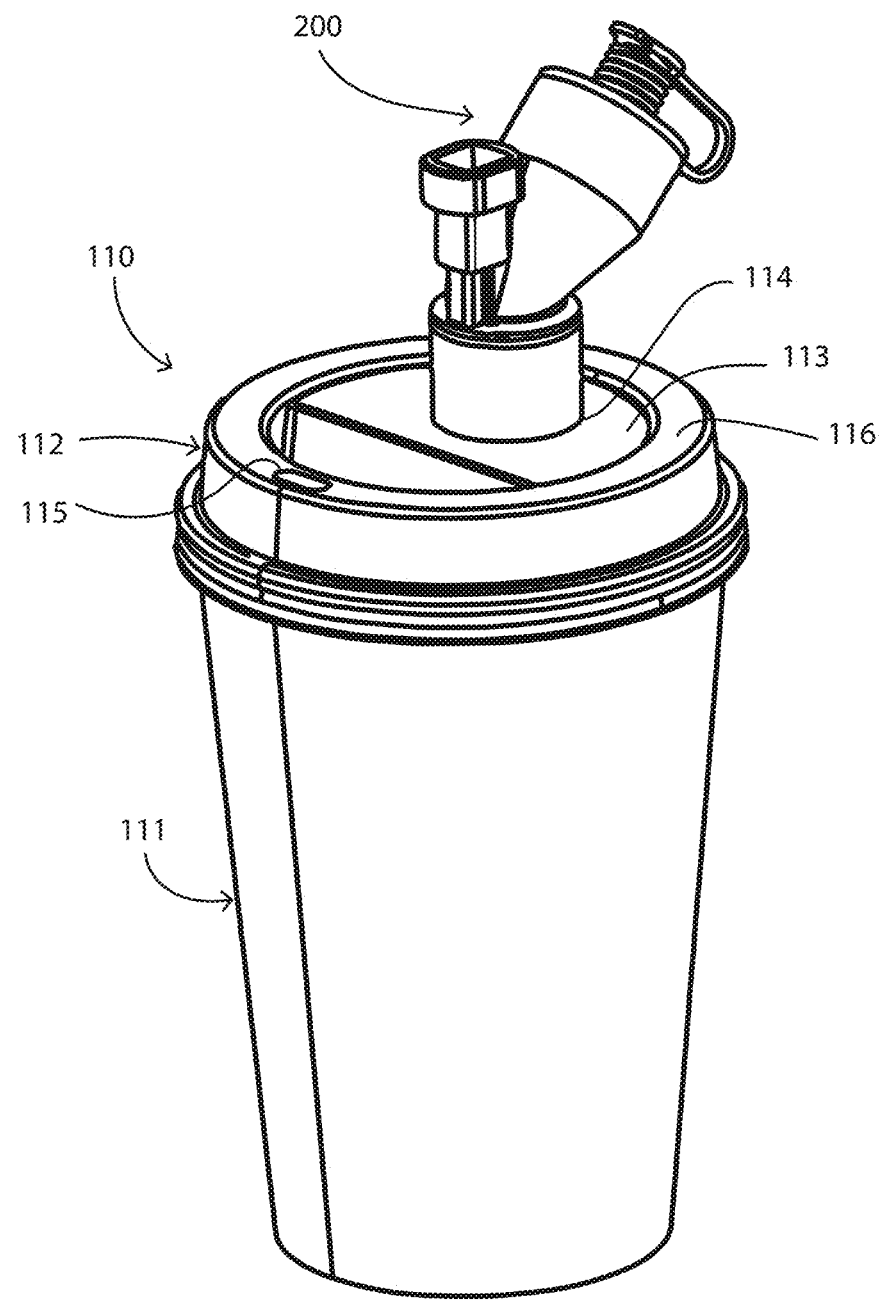
FIG. 2 is a perspective view showing delivery of aerosol from a nebulizer into a disposable chamber by the vaccine station of FIG. 1.
Figure 3:
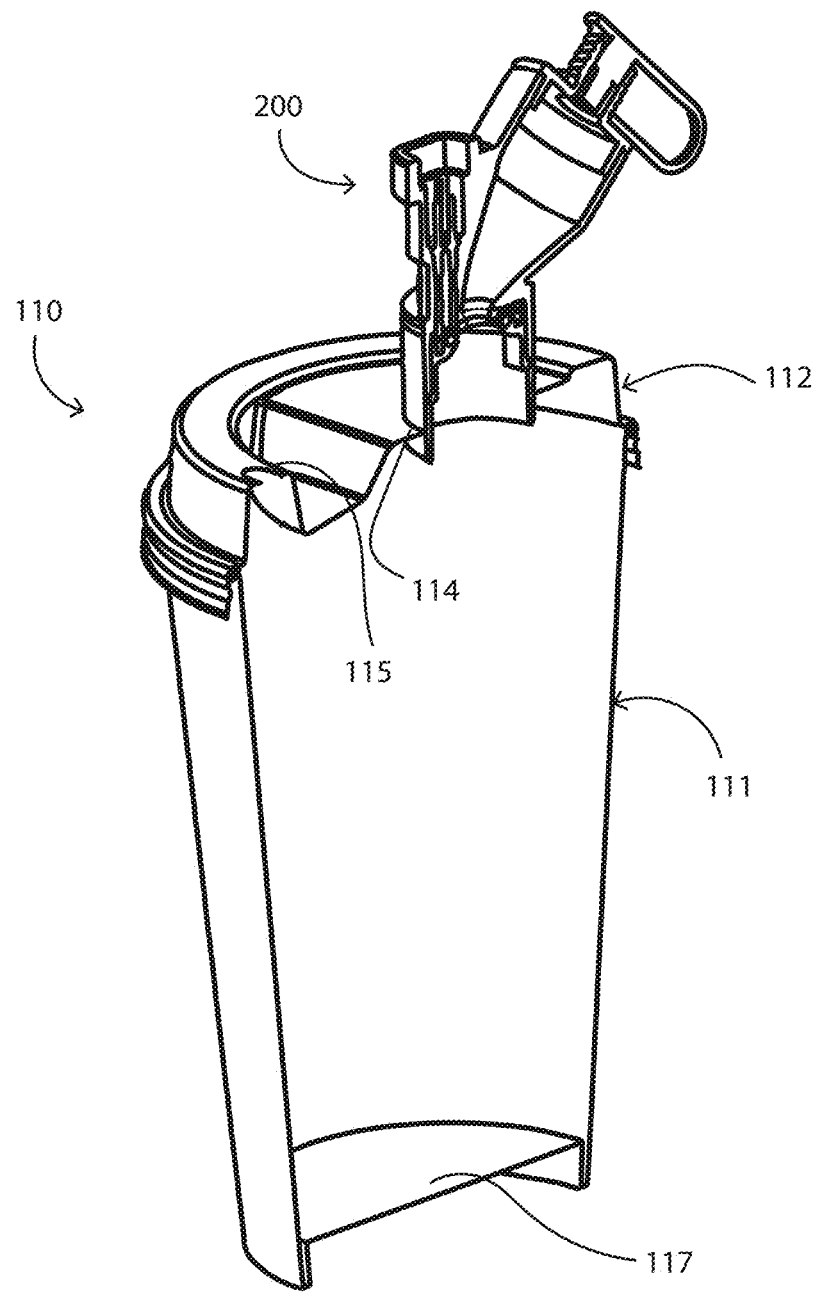
FIG. 3 is a cut-away view showing the chamber and the nebulizer engaged with it.
Figure 4:
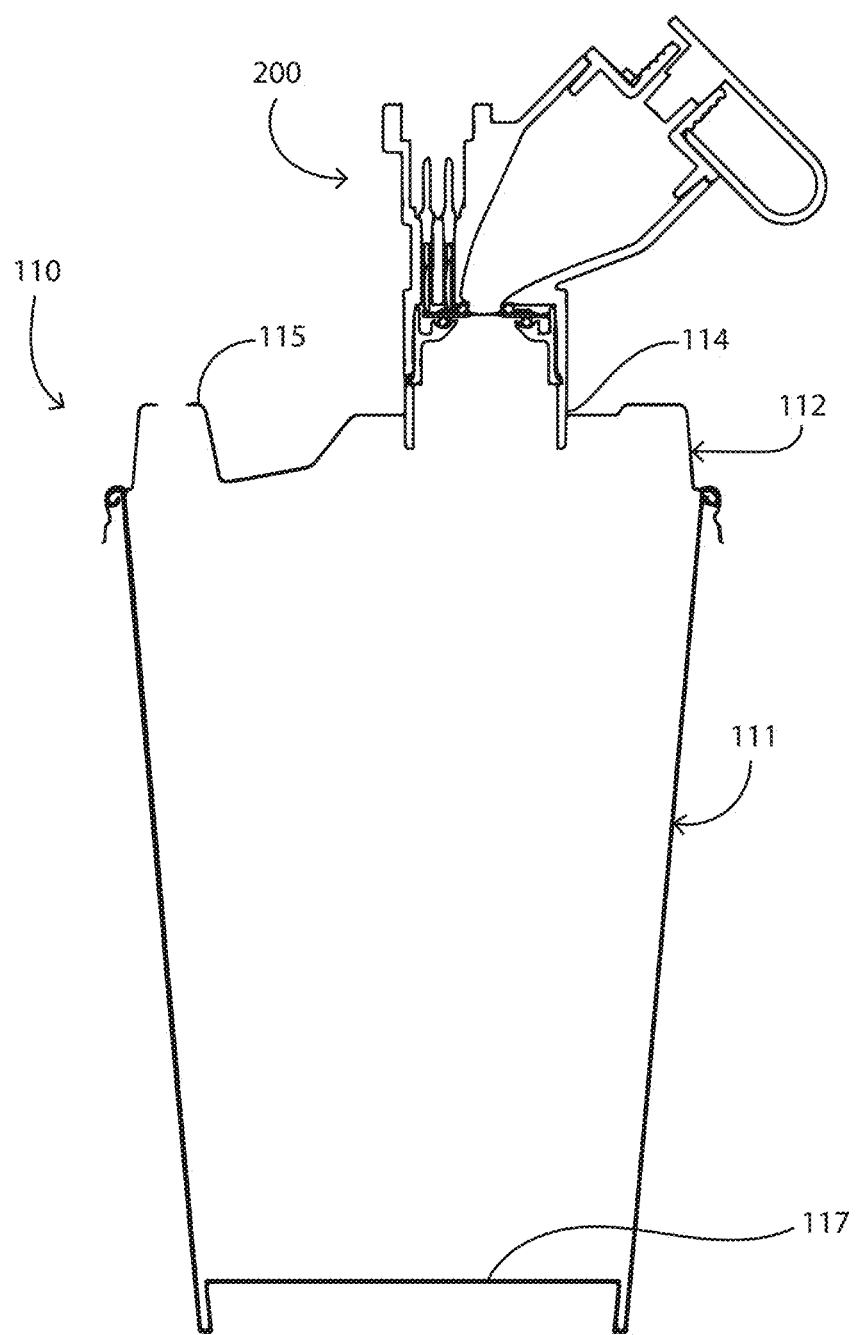
FIG. 4 is a side view of the chamber and nebulizer.

Referring to FIGS. 2 to 4 a chamber 110 is filled in the dispenser 104 by a nebulizer 200 which may be of the type described in our WO2012046220, the contents of which are incorporated by reference. This nebulizer has a vibrating aperture plate mounted to a washer on which there is a piezoelectric actuator which vibrates at about 128 kHz. It is of the type marketed by Aerogen™ under the name Solo™. The aerosol is delivered through an outlet conduit and through the nebulizer delivery port 114 as shown most clearly in FIG. 4.

Liquid to be aerosolised is received at a first upper surface of the vibrating mesh aperture plate and the piezoelectric actuator is activated. Aerosolised liquid is generated at the lower surface of the aperture plate by ejecting droplets of liquid upon activation. The apertures in the aperture plate are sized to aerosolise the liquid such that the majority of the droplets have a size of less than 6 μm. The aperture plate is dome-shaped in geometry. Electrical power is supplied to the piezoelectric actuator by conducting pins. The support washer supports the aperture plate across its central aperture and supports the piezoelectric actuator, and it engages against upper and lower resilient seals for uniform support to help achieve consistent operation of the aerosol generator, with reduced risk of fatigue and a predictable plate vibration response to the applied electrical drive.

End of Dose Detection

For each dispensing operation a pump delivers the liquid into the reservoir of the nebulizer, the quantity being only enough for one dose. Reliability of the nebulizer 200 is assisted by the controller having an automatic end of dose detector, thereby preventing operation of the nebuliser when dry. In one example this is achieved by a method of operation as described in our published PCT Specification No. WO2017/055166, the contents of which are incorporated herein by reference. The method is performed by the aerosol generator of a controller performing the steps of:

measuring aperture plate drive current at each of a plurality of measuring points in a scan, each measuring point having a drive frequency;

determining a minimum value of the drive current in said scan;

determining a value for maximum rate of change of drive current during the scan; and using the minimum value in combination with said maximum rate of change value to execute an algorithm to calculate an indicator value for end-of-dose.

In one example, the controller utilizes the ratio of maximum slope value and the minimum parameter value to provide said indicator. Preferably, in one example the controller multiplies the ratio or a value derived from the ratio by a constant value to provide the indicator. In one embodiment, the controller performs the scan across a frequency range of 128 kHz to 165 kHz. Preferably, the controller initiates the scan in response to a trigger of possible end of dose.

In one example, the trigger is a short scan with a smaller number of measuring points and which detects a change of drive current above a threshold. In one embodiment, the drive current threshold change is above 5 mA, and preferably about 8 mA. In one example, a minimum value of drive current which is approximately less than 30% of a minimum value of drive current of a scan for a wet state of the aperture plate is determined as being indicative of end of dose. This may for example contribute to the trigger from the short scan of possible end of dose, and it may be the sole trigger event. In a preferred example, the method comprises the step of the controller automatically stopping operation of the actuator upon detection of end of dose.

Reservoir Layer Aperture Plate

In various examples, the nebulizer aperture plate is manufactured by photo-defined manufacturing process as described in our published PCT Specification No. WO2013/186031, the contents of which are incorporated herein by reference, to have an upper reservoir layer with liquid supply cavities and a lower layer of aerosol-forming apertures. There may for example be in excess of 2500 aerosol-forming apertures per square mm.

The diameters of the liquid supply cavities are chosen such that a pre-determined number of droplet-size forming apertures are exposed, which determines the number of active holes and thus defines the quantity of liquid being aerosolised per unit of time. The size and number of holes in both layers is selected to achieve the desired ranges of droplet size and flow rate distribution.

The following is a table of examples of different configurations for aperture plates (APs) of 5 mm diameter:

| | | | | |
|---|---|---|---|---|
| Liquid supply Cavity Diameter (mm) | 0.10 | 0.08 | 0.06 | 0.04 |
| Number of Cavities | 815 | 1085 | 1464 | 2179 |
| Number of apertures per Cavity | 12 | 7 | 4 | 1 |
| Apertures per AP | 9780 | 7595 | 5856 | 2179 |

This "reservoir layer" arrangement of overlying liquid supply cavities makes it possible to more consistently achieve smaller and more controllable particle/droplet sizes in the range of 2 µm to 4 µm. It also makes it possible to more consistently achieve higher flow rates, in the range of for example 0.5 ml/min to 2.5 ml/min, more typically 0.75 ml/min to 1.5 ml/min.

A reservoir layer is particularly suited to aerosolization of liquids with certain surface tensions and viscosities, as described in WO2016/198667, the contents of which are herein incorporated by reference. In particular the liquid to be aerosolized preferably has a viscosity in the range of 1 to 15 cP and a surface tension in the range of 0.5 mN/m and 72 mN/m, and it is preferred that the output rate is at least 0.01 ml/min. As noted above the flow rates are more particularly preferred as being in the range of for example 0.5 ml/min to 2.5 ml/min, more preferably 0.75 ml/min to 1.5 ml/min The aperture plate may have in the region of 60,000 aerosol-forming apertures, and these are preferably supplied by liquid supply cavities in a reservoir layer.

Single Dose Aerosol Chamber

The aerosol chamber 110 is a single use/dose device for delivery of a single dose of aerosol. At a general level, without close user scrutiny, and it has the overall appearance of a disposable beverage cup. This assists with its use, as it is intuitive for a user to consume the aerosol in a manner akin to drinking a beverage in terms of how it is handled. The chamber 110 has a container of a generally tubular side wall 111 which narrows by being tapered inwardly towards a base 117, and a lid 112. The lid 112 comprises a central wall 113 with a round opening 114 substantially matching the external diameter of the outlet of the nebulizer 200. This is a nebulizer coupling or delivery port, alternatively referred to herein as an aerosol inlet. There is an inhalation port 115 in a raised rim 116, near the side diametrically opposed to the nebulizer delivery port 114.

Nebulizer Delivery Port of the Single Dose Aerosol Chamber

In this case the diameter of the nebulizer delivery port is 24 mm, matching an outlet conduit of the aerosol generator which is ISO 5356 compliant with an internal diameter of 22 mm. This gives an area of about 450 mm$^2$. In general, it is preferred that the nebulizer delivery port has a diameter in the range of about 6 mm to 30 mm giving areas in the range of 30 mm$^2$ to 700 mm$^2$. However, where it is important that the aerosol efficiently reaches the lungs (which is not necessarily so important for vaccines) then we have found that a smaller nebulizer port is advantageous, preferably having an area at the lower end of the above range, preferably 30 mm$^2$ to 120 mm$^2$. The nebulizer delivery port has two functions, namely (a) delivery of aerosol in the delivery apparatus, and (b) acting as a vent during inhalation. If its area is in the lower end of the above range then there is less inflow of air into the chamber during inhalation and hence more efficient delivery through the mouth or nose and down into the bronchi and bronchioles. For such a nebulizer delivery port the nebulizer may have a conduit which narrows from a standard 22 mm diameter to the relevant size. Also, for such uses it is preferred that there is no opening other than the inhalation and nebulizer delivery ports, and so the sole vent opening during inhalation is the nebulizer delivery port.

Other Features of the Single Dose Chamber

The aerosol outlet delivery/inhalation port 115 is in a raised rim 116, akin to that of a beverage cup drinking aperture. The volume of the chamber 110 is preferably in the range of 100 mL to 600 mL, more preferably in the range of 150 mL to 400 mL. This volume is sufficient for a single dose which can be inhaled in a single breath via the inhalation port 115. The material of the chamber is paper-based or plastics (preferably recyclable). The material preferably has good thermal insulation in order to reduce rainout on the internal surfaces. The container 111 has a curved wall which tapers to narrow downwardly towards a planar base.

Advantageously the nebulizer delivery port 114 and the inhalation port 115 are each off-centre, adjacent the container 111 wall on opposed sides of the container, and are also preferably generally in the same plane. This contributes to effective flow of aerosol into the container 111 in stage 2, and subsequent flow out during inhalation, as described in more detail below. It is advantageous that the inhalation port 115 has a curved oblong shape extending substantially circumferentially, because this makes it easy for a user to inhale in a manner analogous to drinking a beverage from a disposable cup.

The nebulizer 200 of the dispensing stage 104 is calibrated with a flow rate to deliver the required dose in a specified time during which its outlet is engaged with the nebulizer delivery port 114. There is delivery of a liquid single dose into the reservoir of the nebulizer and there is aerosolization until sensed end of dose. The controller of the nebulizer may stop and start according to detection of presence of a chamber 110 engaging the nebulizer 200 outlet. In either example, the station 100 is perceived by the user to work like a beverage dispenser, with picking or automatic delivery of a "cup", filling and removal of the filled "cup", inhaling its contents and disposal of the empty "cup".

There is no need for a valve to close off the nebulizer delivery port because the chamber will typically be held upright and the contents will be inhaled within a minute. The analogy with a hot beverage dispenser helps because the users will naturally tend to keep the chamber upright as they would a cup.

In one example the chamber is fully or partially translucent, for example with a window akin to that of an envelope, to allow viewing of the aerosol for reassurance that it is present and that it has been inhaled completely.

While there is no valve for the chamber inlet in this example, in other examples there may be one. If so, it may be very simple, merely a flap of lid material which is resiliently hinged to return to close the opening after the nebulizer is disengaged. This arrangement utilizes the living spring' properties of the lid material to deflect and close the opening before inhalation, and open slightly to assist flow-through during inhalation. If it is hinged on a side closer to the edge then it will guide flow towards the centre of the container during inhalation, or if hinged on a side further from the wall it may guide flow towards the wall during inhalation. The location of the hinge can be chosen according to the preferred vent-assisted flow dynamics during inhalation.

Dispensing Method Features and Attributes

It will be appreciated that the invention allows a very large number of people to be administered with an aerosol such as a vaccine in a short period of time. The fact that the dose will not be very accurate is not a problem because it is only required that there be a minimum volume for applications such as vaccination.

The chamber size is optimized dependent on the dose required and to minimise the time between starting the aerosol 'fill' to patient inhalation to reduce aerosol loss through "rain-out" sedimentation and impaction.

In other examples the chamber is of a single piece of material which is folded to provide the lid. Beverage cups of such construction are known, and indeed it is an advantage of the invention that it can utilize the benefit of advances in beverage cups in terms of their ease of safe recycling and thermal insulation properties and stacking and transporting to minimise the footprint associated with their use.

It is preferred that the droplet size be small, preferably with at least 80% of droplets being less than 6 µm. This may be achieved using a vibrated aperture plate which has characteristics of being manufactured with a photo-defined process for the aerosol-forming holes, such as described in WO2013/186031 (EP2859137B). In this case there is a reservoir layer of cavities each of which is over a number of aerosol-forming apertures. The cavities may have a diameter in the range of 20 µm to 400 µm, and the aerosol-forming apertures may have a diameter in the range of 0.5 µm to 10 µm, preferably 0.5 µm to 6.0 µm. Such arrangements help to achieve small droplet sizes, thereby helping to optimise delivery into the lungs and minimizing rainout on the chamber internal surfaces.

However, depending on the nature of the agent being administered, it may be desirable to deliver larger droplets for access to either the user's upper airways or potentially to the nasal cavity. Such larger droplets may have a size distribution in the range of 6 µm to 10 µm, or greater than 10 µm.

As shown in FIG. 1 there is a simple three-step procedure for vaccination of a person. The first step may be replaced by a user instruction to the station which causes an automated placement and filling of a chamber without user handling.

Referring to FIGS. 5(a) to (g) inclusive it will be apparent that there are major benefits in the nebulizer delivery port and the inhalation port being adjacent opposite sides of the chamber, as it benefits from the Coanda effect. In these images the lighter shade indicates greater concentrations of aerosol.

Figure 5A:
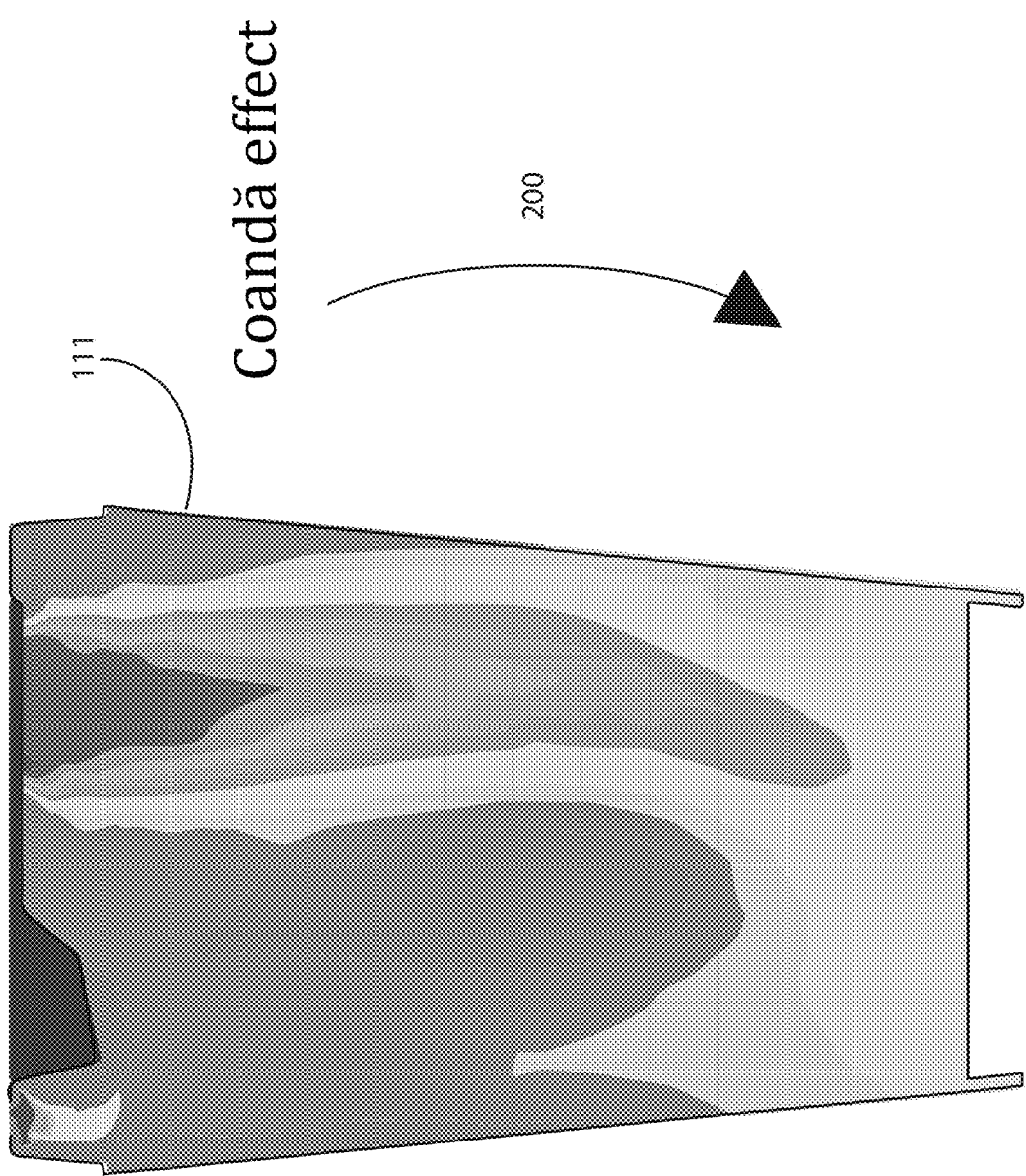
Figure 5B:
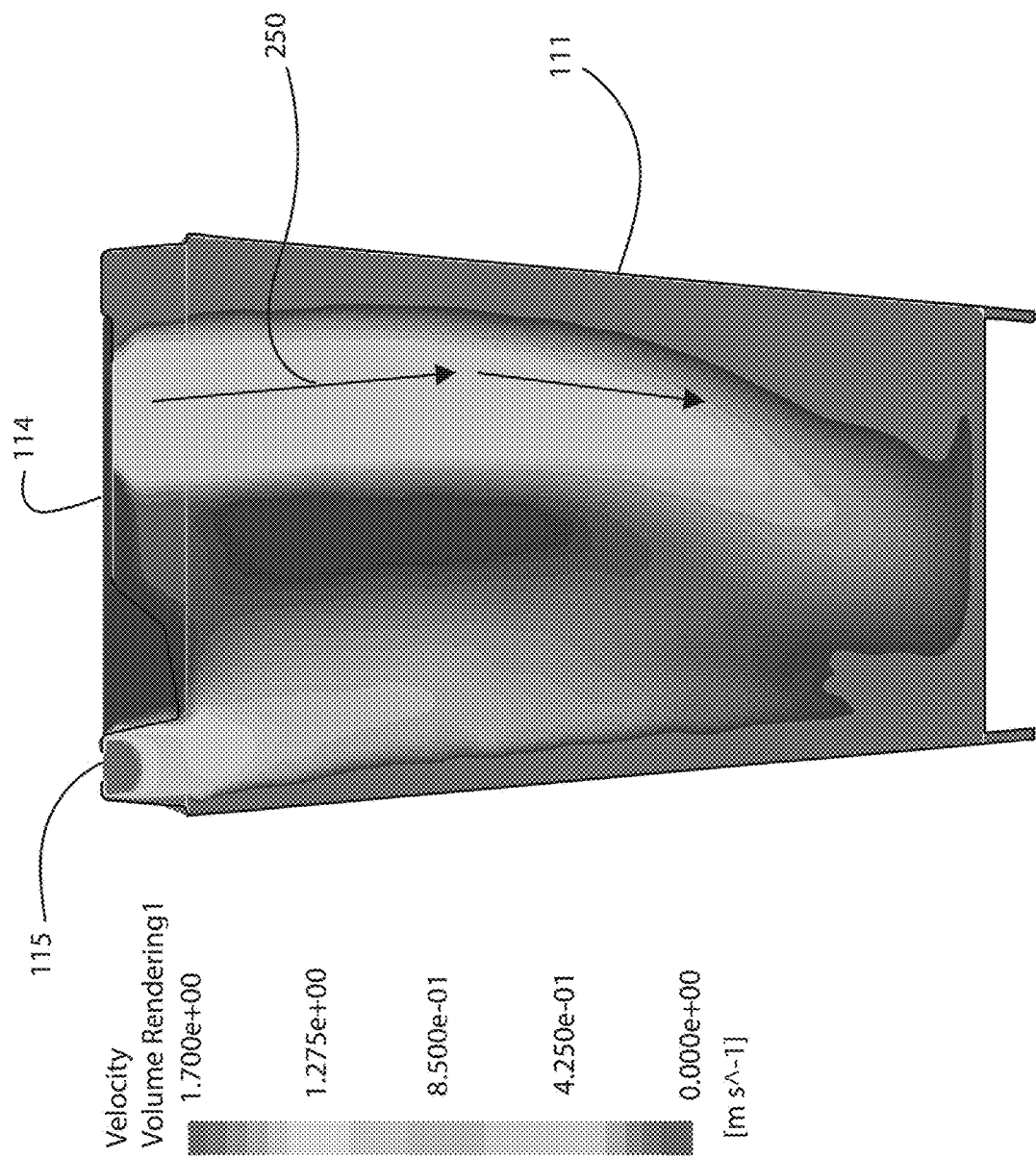
Figure 5C:
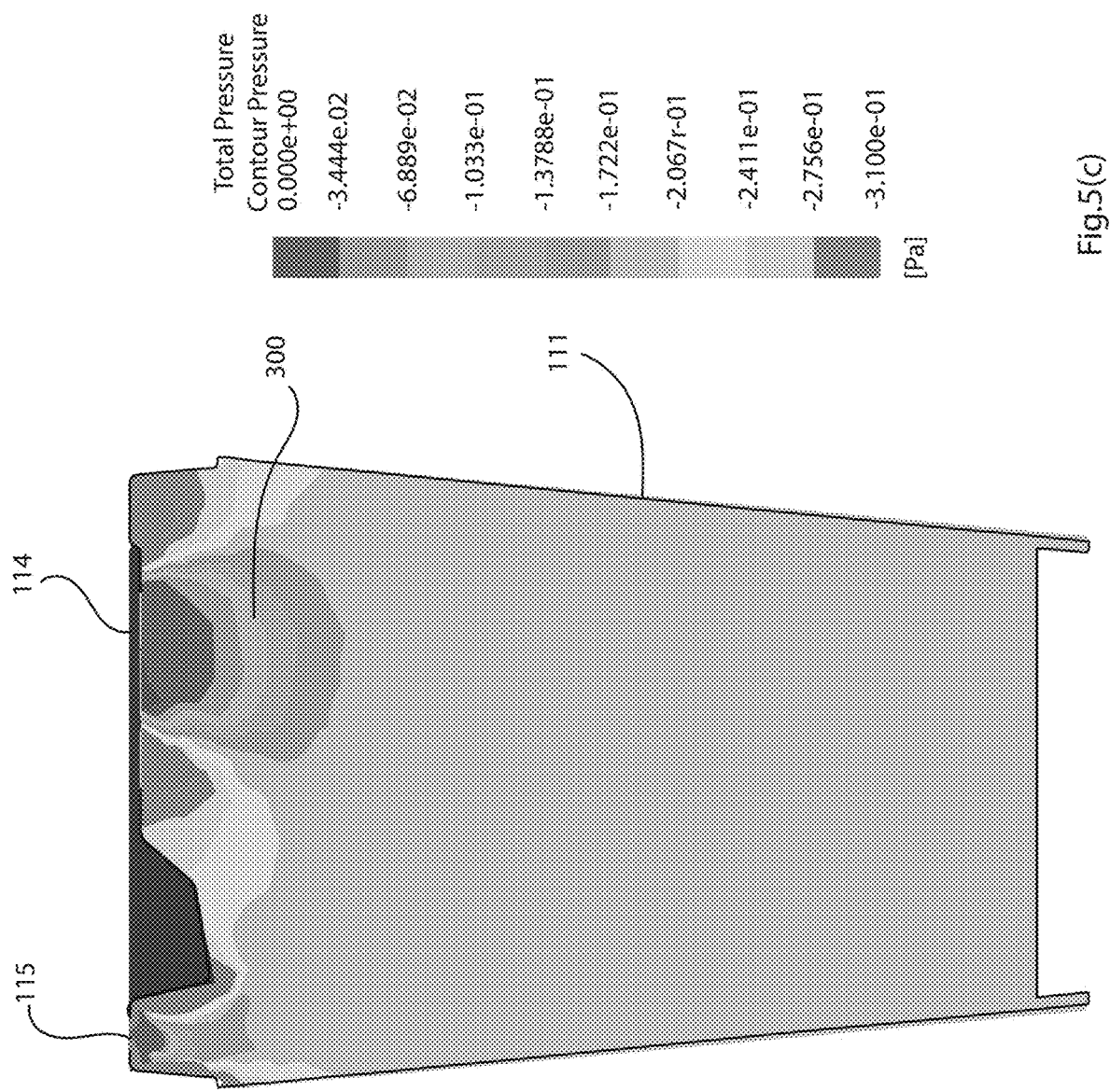
Figure 5D:
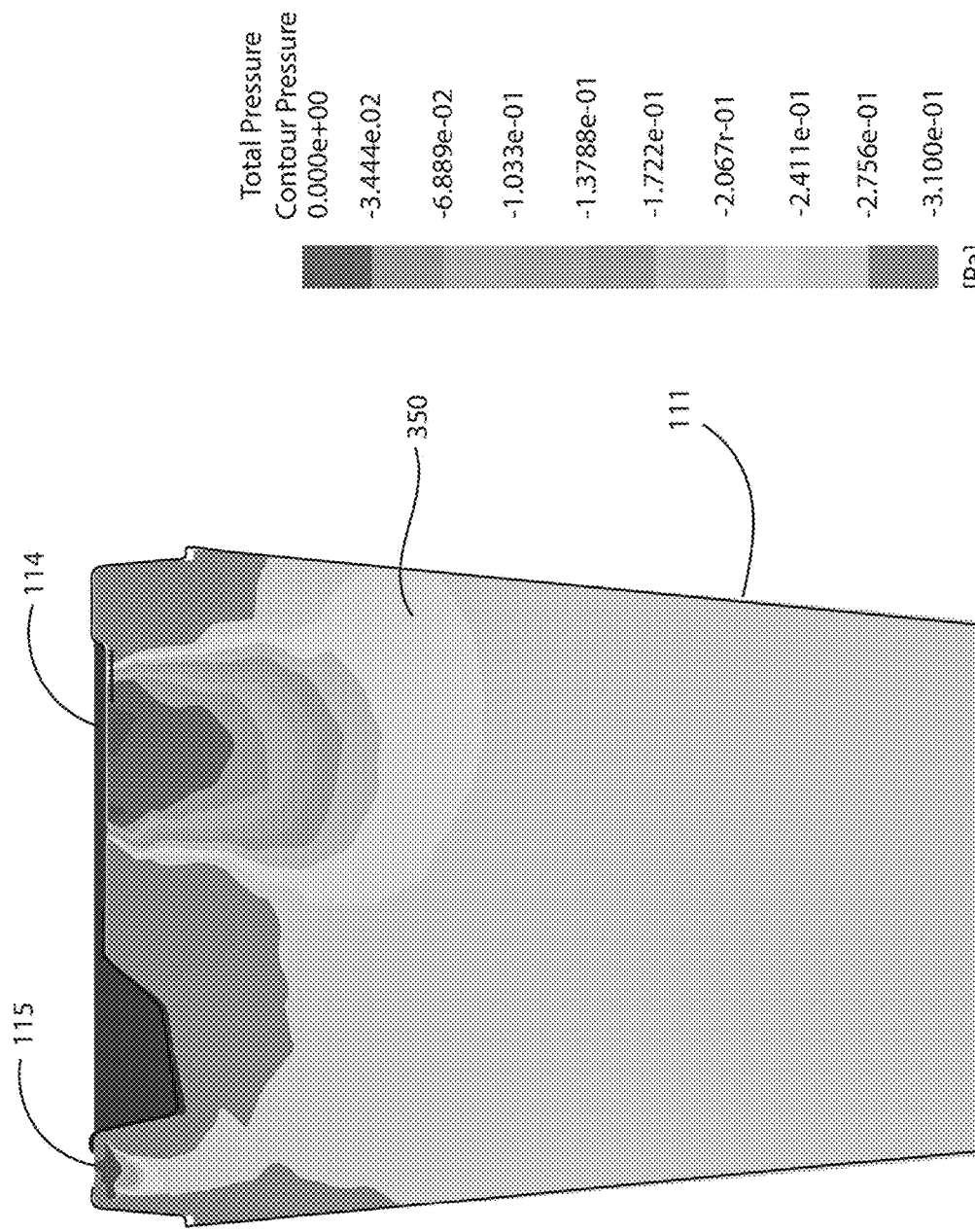
Figure 5E:
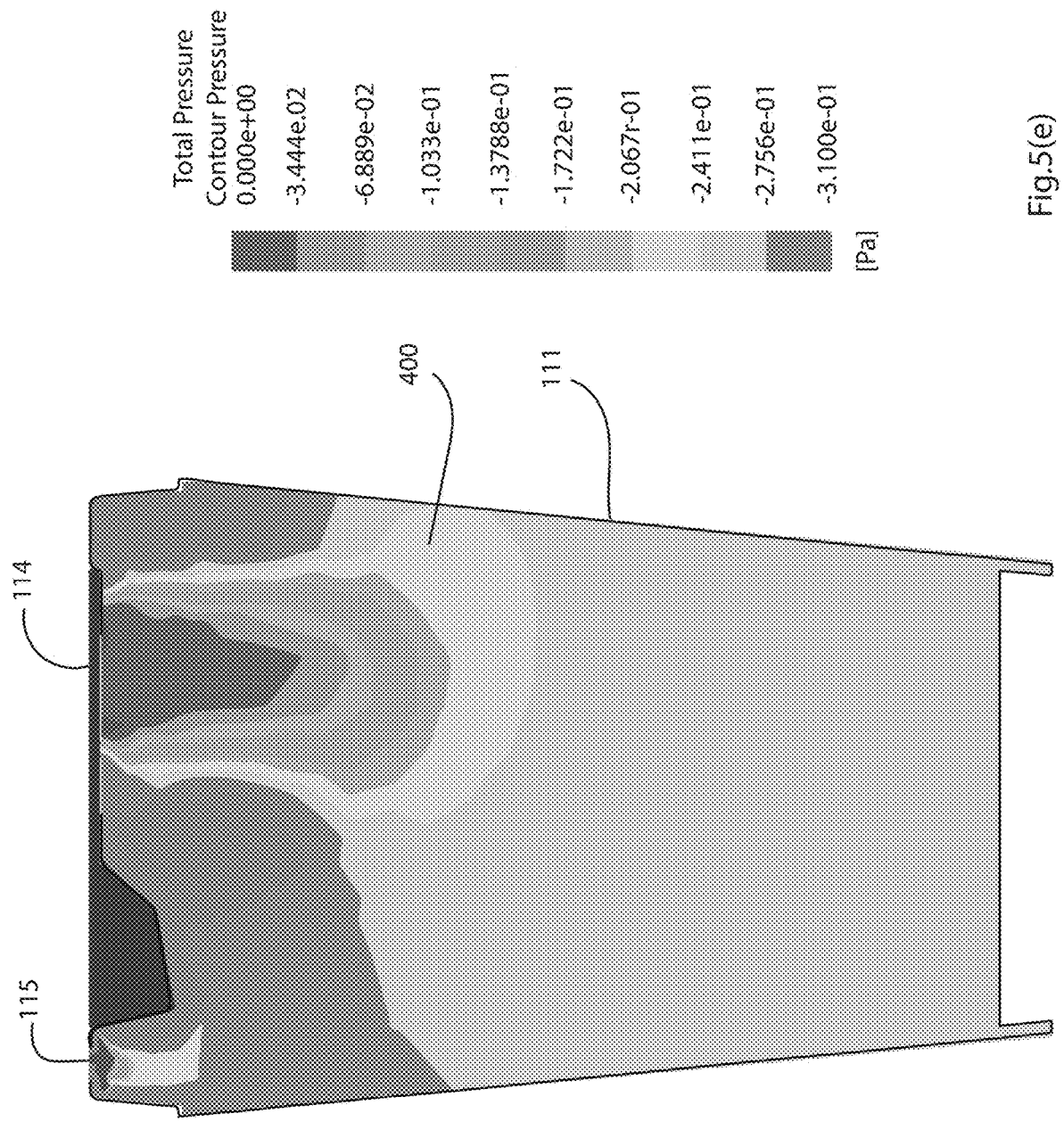
Figure 5F:
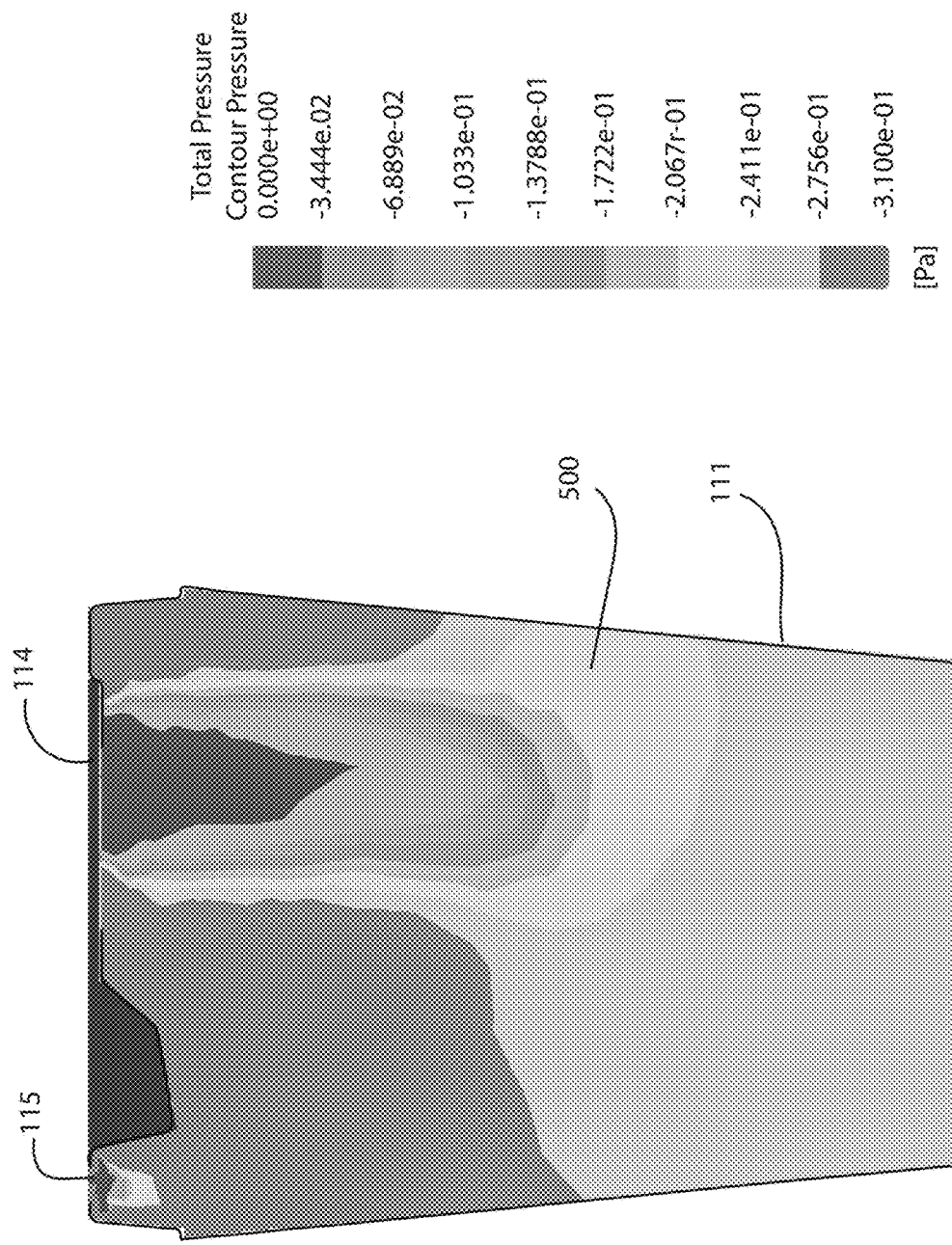
Figure 5G:
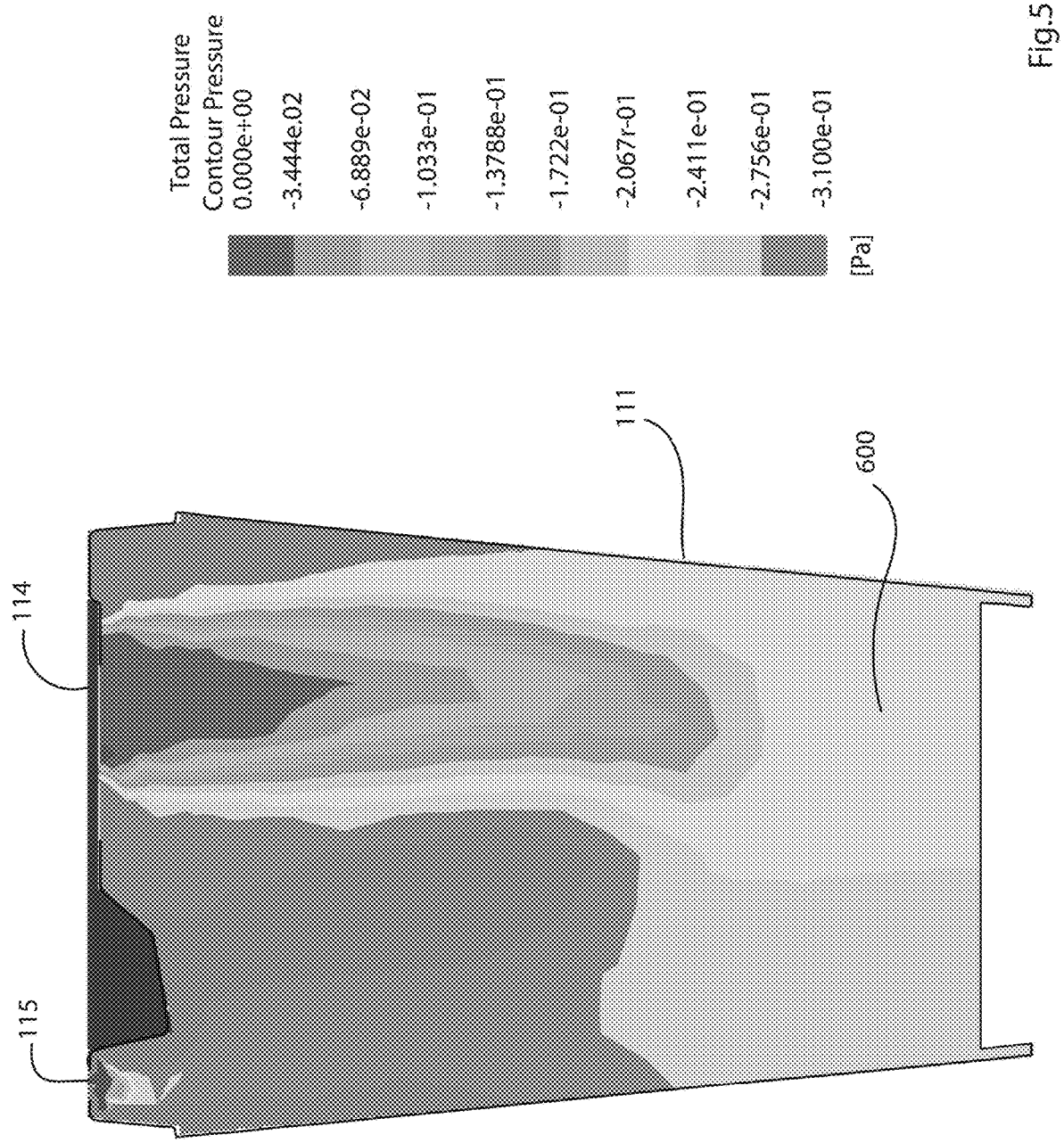

FIG. 5(a) shows that placement of a hole in proximity to walls promotes the Coanda effect with an arrow 200 indicating the general flow pattern, downwards and back upwards towards the outlet 115. Placement of the mouth opening in proximity to the walls promotes the Coanda effect and promotes flow of air deeper into cup. FIG. 5(b) shows flows as arrows 250, with velocities of up to 1.2 m/s in localized volumes near the side wall. FIG. 5(c) shows an early stage of the fill as aerosol 300 enters via the delivery port 114, with pressures up to about 0.2 Pa. FIG. 5(d) shows progression of aerosol 350 downwards, FIG. 5(e) shows further downward flow 400, FIG. 5(f) further flow 500 downward filling a larger volume towards the bottom of the chamber, and FIG. 5(g) shows a flow 600 reaching the bottom of the chamber 111.

As shown in FIGS. 5(b) to 5(g) proximity to the wall creates a low-pressure imbalance which tends to draw the aerosol stream towards the wall. These images show progress of the filling aerosol. This benefit is achieved by the fill opening being adjacent the wall of the container 111. It is also advantageous that the inhalation port 115 is adjacent an opposed side of the chamber.

It will be appreciated that the invention achieves low velocity aerosol dispensing with minimising impaction and maximising dwell time of the aerosol in the container. By use of photo-defined aperture plate with a reservoir layer ("PDAP") in the nebulizer there may be consistently a lower volumetric median diameter (VMD) with higher plume density and higher flow rates, minimising potential settling time in the container i.e. shorter time to deliver more and with lower VMD will maximise dwell time of the aerosol. The shape and size of inhalation port, being oblong in the circumferential direction and similar to a drinking outlet in a disposable beverage cup, makes it more user-friendly for inhalation.

There may be a hydrophobic coating on at least some of the inside surfaces of the chamber, thereby reducing attraction of aerosol to the walls and lid of the container, decreasing impaction on the surfaces and increasing available aerosol to the recipient.

It is envisaged that the chamber may have only a single port, for both nebulizer delivery and inhalation, thereby minimising a risk of cross-contamination. However, it is preferred that there be two as this will assist flow out during inhalation and the sizes can be optimized. There may be a transparent material or a window in the chamber to allow for visibility. The dispense mechanism preferably has proximity sensors to detect chamber presence to allow for automation and fixed dose delivery. Electronic drive control of the nebulizer can achieve a desired aerosol flow rate, preferably for chambers for many applications having a volume of about 300 mL+/−50 mL. The nebulizer is preferably configured for delivery in less than 15 seconds, and time to inhalation is preferably less than 10 seconds after dose finishes aerosolising.

The method and apparatus find use in mass vaccination programs requiring small unit volumes of vaccine to be delivered at an economic price. It is particularly applicable where small volume doses can utilise circa 0.1 mL (between 0.05 mL and 0.25 mL) as aerosol losses between fill and administration will be reduced.

Paper can be used as the primary material of the chamber, but clear plastics cups have the advantage of visual confirmation that aerosol dose has been taken. The invention makes use of extremely low cost and available manufacturing resources for very high-volume components such as the chamber.

It has been found in tests that the following inhaled doses were achieved in adult human subject testing: (12 adults. Mix of 7 Male and 5 Female. 3 doses each maximum 5 second delay to inhalation from end of dose, 0.1 mL dose, max 2 sec inhalation time). The overall average inhaled dose was 34.39%±1.50% (36 runs in total).

| Subject | Inhaled Dose (%) AVG | Standard Deviation, STDEV |
| --- | --- | --- |
| #1 | 34.10 | 0.17 |
| #2 | 33.52 | 0.89 |
| #3 | 36.42 | 0.73 |
| #4 | 33.62 | 1.76 |
| #5 | 37.10 | 0.87 |
| #6 | 36.23 | 1.61 |
| #7 | 34.39 | 0.73 |
| #8 | 34.30 | 1.60 |
| #9 | 32.85 | 1.49 |
| #10 | 33.33 | 1.26 |
| #11 | 32.17 | 1.05 |
| #12 | 34.68 | 0.89 |
| AVG | 34.39 | |
| STDEV | 1.50 | |

A smaller droplet size aerosol is preferred. Smaller droplets provide gains with respect to:
inhaled dose
sensitivity to delay to inhalation

| | Dose volume (mL) | Delay (sec) | Inhaled Dose (%) AVG | STDEV |
|---|---|---|---|---|
| Very Low VMD (2.6 μm) | 0.1 | 1 | 30.24 | 0.88 |
| | 0.1 | 5 | 28.89 | 0.89 |
| | 0.1 | 10 | 27.44 | 0.73 |
| | 0.2 | 1 | 28.75 | 0.36 |
| | 0.2 | 5 | 27.97 | 0.29 |
| | 0.2 | 10 | 27.05 | 0.22 |
| Low VMD (3.38 μm) | 0.1 | 1 | 28.80 | 1.17 |
| | 0.1 | 5 | 27.25 | 0.58 |
| | 0.1 | 10 | 24.25 | 0.33 |
| | 0.2 | 1 | 18.55 | 0.29 |
| | 0.2 | 5 | 17.97 | 0.15 |
| | 0.2 | 10 | 17.25 | 0.52 |
| Mid VMD Neb (4.62 μm) | 0.1 | 1 | 28.02 | 1.89 |
| | 0.1 | 5 | 24.64 | 0.77 |
| | 0.1 | 10 | 18.65 | 0.60 |
| | 0.2 | 1 | 18.55 | 1.09 |
| | 0.2 | 5 | 15.03 | 0.17 |
| | 0.2 | 10 | 13.53 | 0.51 |
| High VMD Neb (6.32 μm) | 0.1 | 1 | 25.70 | 0.73 |
| | 0.1 | 5 | 19.42 | 1.00 |
| | 0.1 | 10 | 15.36 | 0.29 |
| | 0.2 | 1 | 15.94 | 0.38 |
| | 0.2 | 5 | 12.85 | 0.17 |
| | 0.2 | 10 | 11.11 | 0.22 |

In some examples and, where facilitated by formulation design, a range of dose volumes may be used, with smaller dose volumes providing greatest inhaled dose.

| Dose Volume (mL) | Delay (sec) | Inhaled Dose (%) AVG | STDEV |
|---|---|---|---|
| 0.1 | 1 | 26.86 | 1.31 |
| 0.1 | 5 | 21.45 | 1.16 |
| 0.1 | 10 | 20.10 | 0.44 |
| 0.2 | 1 | 17.39 | 0.53 |
| 0.2 | 5 | 14.40 | 0.36 |
| 0.2 | 10 | 11.69 | 0.44 |
| 0.05 | 1 | 32.46 | 1.74 |
| 0.05 | 5 | 26.48 | 1.34 |
| 0.05 | 10 | 21.64 | 0.89 |

In some examples, the users may take multiple smaller doses with breaths in-between (for example 0.05 mL, breath, 0.05 mL, breath, giving a total 0.1 mL dose in 2 breaths (max 39.08%). In other examples there was a 0.2 mL dose in 4 breaths (max 41.32%)) for an increased dose. Advantageously, the controller can be programmed to provide the relevant user instructions, which of course are at the point of delivery. More examples are provided in the table below.

| Total Dose Vol (mL) | Delay (sec) | Inhaled Dose (%) AVG | Stdev | Test conditions |
|---|---|---|---|---|
| 0.2 | 1 | 32.93 | 1.21 | 0.2 ml delivered –> 1 breath |
| 0.2 | 1 | 51.15 | 1.60 | 0.1 ml inhale --> Neb 0.1 ml inhale |
| 0.2 | 5 | 47.47 | 2.76 | 0.1 ml delivered wait 5 secs–> Neb removed from port for first breath –> replaced and another 0.1 ml delivered wait 5 secs –> neb removed for seconds breath |
| 0.2 | 1 | 60.98 | 1.15 | Neb on for 5 secs--> stopped--> breath in--> neb on for another 5 secs --> stopped --> breath in --> repeat until end of dose |

The invention also has applicability for paediatric patients. For example, assessing a 155 mL tidal volume, we note maximum 10.91%, however adopting the other dosing strategies outlined herein (for example droplet size, mouthpiece design etc) may increase that inhaled %.

It is envisaged that there may be a one-way valve in the container base (opposite the mouthpiece) allowing air flow into the chamber for better clearance. There may be one or a number of apertures in the base to allow for air inlet for better clearance. The controller may be configured to provide via the instruction screen 103 advice of a maximum number of breaths/inhalations, for example it may stipulate a maximum of 2 breaths. It may also advise a short inhalation. The nebulizer may have a drive configured for unusually high flowrate outputs, such as by high voltage (faster flow rate) or pulsed control (softer plume, lower density aerosol).

The chamber internal surfaces may have a hydrophobic coating or texture to repel suspended aerosol droplets. There may be an antimicrobial coating on the outside of the chamber to prevent cross contamination from handling. The chamber or apparatus may have features to reduce aerosol emissions post nebulisation. For example, a filter or cover may be attached to the aerosol generator port to close over it after the chamber is removed (reason: reduce emissions which may be a safety or regulatory concern). For example, it may be mounted as a flap which is pushed open during filling by an actuator and springs into a close position upon removal from the aerosol outlet. There may be additional openings in the chamber to ensure that pressure within the chamber does not increase more than is desired during the filling process. The mouthpiece 115 performs this function, but one or more small additional vents may also assist. The presence of such vent openings is a function of the expected pressure of delivery. The mouthpiece may be oval, round, oblong, to aid in the efficiency of the aerosol delivery. The lid may have a protruding, indented or flat mouthpiece for delivery of aerosol.

The nebulizer may be of any type suited to aerosolization of a dose within a period of less than one minute. It is preferred that it be of the type having a vibrating mesh, such as the Aerogen Solo™ nebulizer, particularly because such a nebulizer provides a very fine aerosol with a consistent size in the range of 1 μm to 6 μm. However, depending on the surface tension and viscosity of the liquid being aerosolized the aerosol generator may alternatively be of the surface acoustic wave, pressurised metered dose inhaler, actuated dry powder inhaler, compressed air-driven venturi, or Electro Hydro Dynamic Atomization types.

The dispensing apparatus may be linked by a conduit to a remote nebulizer, or it may have the nebulizer locally but connected by a conduit to the aerosol outlet. Also, the dispensing apparatus may be part of a group of apparatus' for which a central controller provides high-level control, each apparatus being for example in a booth.

The material of the chamber is preferably insulating to the extent of prevention of condensation, and it is also preferably inexpensive and recyclable. An example of such a material which is suitable for high-speed laser processing is polystyrene. The chamber may have an outlet suited to inhalation via the nose. This may include soft and moulded materials that conform to or surround the features of the adult, paediatric or infant nose, because vaccines may also be targeted to the nasal cavity as well as nasal passages and lung in order to elicit an immune response and/or deliver a therapeutic agent such as a steroid (budesonide), interferon (antiviral), flumist (vaccine).

A face mask may be attached to the chamber, as it may allow nose and lung delivery, especially for children. The chamber may have multiple ports for inhalation, for example two holes for nasal inhalation. The aerosol port is preferably located close to the edge for the reasons given above, to encourage flow down the container wall. However, it is envisaged that it may be positioned close to the centre, for ease of automation.

The dispensing apparatus may be adapted for delivery of a wide variety of formulations including, but not limited to, vaccines, antivirals, antibodies, bronchodilators, mucociliary beat modulators, hallucinogens, or recreational inhalants.

Desktop Dispensing Apparatus

The dispensing apparatus may take the form of a smaller configuration, such as for placing on a desk or table. An example of such an apparatus, 500, is shown in FIGS. 6 to 14. The apparatus 500 comprises a housing 501 having lifting handles 520 and with a top light emitter 510 which is controlled to emit with a desired colour to indicate the stage, such as red for the duration of dispensing and green for when a filled chamber is ready to be removed. There is a display screen 511 immediately below the light 510, and beneath that there is a dispensing stage with an automated chamber handler 512 with an interlock function. The general operation of the apparatus 500 is akin to that of the apparatus 1, but it is smaller and more convenient in some circumstances.

The chamber handler 512 comprises a chamber-receiving annular receiver 530 having a housing 531 and a ring 532 of limit switches to detect presence of a chamber in the receiver and whether it is concentric. The receiver 530 is at one end of an arm 533 which is rotated by a motor drive 535 in multiple cycles through 180°. The other end of the arm 533 supports a curved cover 540 having a radius of curvature of the radius of the arm 533. It is the outside surface of the cover 540 which is visible in the ready-for use-configuration shown in FIG. 6. This acts as an interlock, preventing access by the user while a chamber is being filled. The handler 512 is controlled by the digital controller, not shown, which also controls an automated nebulizer 600 which is shown in FIGS. 12 to 13. The nebulizer is supplied by a container 570 and a pump 571, which are linked to each other by tubing and the pump is a peristaltic pump linked by tubing to the nebulizer 600. The automated nebulizer 600 comprises a beam 601 with end carriages 620 and 621 which slide vertically on rails 625 driven by a lead screw drive mechanism. The beam 601 supports an aerosol generator of the type marketed by Aerogen™ under the name Solo™. The cylindrical outlet conduit downstream of the vibrating aperture plate is engaged with a support ring 611 which houses a sensor ring 612 with proximity sensors 615 and beneath which there is a pusher 602 on spring-loaded pillars 603. The sensors 615 are limit switches which detect presence of a chamber in proximity to the pusher 602 and this is interpreted by the controller as sufficient to actuate aerosolization by the aerosol generator 610.

Upon aerosolization for the desired time period, the vibration of the aperture plate ceases, and the beam 601 is lifted, while the pusher 602 retains contact for the length of the sprung pillars 603 to ensure that the lid of the chamber does not lift off or dislodge in any way. Then, the arm 533 is rotated through 180° so that the filled chamber 110 is presented as shown in FIG. 10 to be removed by the user. This is synchronized by the controller with display of instructions on the screen 511.

Alternative Features and Characteristics

It is envisaged that in other examples there is no need for the user to place an empty chamber in the handler, as it may automatically pick it from a nested stack held internally.

The dispensing apparatus 500 is particularly suited to use in remote locations which do not have a developed technical infrastructure.

The dispensing apparatus may include a vacuum system to remove excess aerosol in the environment of the dispensing stage, such as aerosol that may escape during detachment of the chamber from the nebuliser outlet. Such a system may include a disposable filter to reduce emissions for safety purposes.

As noted above, in preferred examples the nebulizer has end of dose detection, and it may have an interface to notify the user and/or supervisor of end of dose or of reduced dose placed on the aperture plate. The end-of-dose detector may include a liquid detection sensor or a feature of the vibration drive to detect end of dose based on vibration characteristics of the aperture plate, such as described in WO2015/010809 (EP3024590B) or WO2017/055166 (EP3356056B).

The controller is preferably programmed to keep records of dispensed agent (for example, vaccine) batch numbers. These may be linked with unique identification of each chamber by way of optical reading a bar or other code. Also, the controller may be programmed with different modes of operation, one mode for each of a plurality of agents being dispensed. The parameters which are controlled include any or all of dosing strategy, volume information, active aperture plate actuation duration. Power may be provided by solar cells, especially for use where mains power is not readily available.

The apparatus is particularly suited to dispense any therapeutic agent that may be administered in a dose volume of about or less than 0.5 mL. It preferably has a status light and/or sound emitter, to inform the next user when to approach the vaccination station. It may have proximity sensors to detect presence of an individual to determine when to commence vaccination. The apparatus may be configured to dispense for pediatric use, in which case the chamber may be of a relatively small volume smaller volume such as 250 mL. There may be an insert as part of the patient interface that, on inhalation, preferentially draws air from the lower end of the chamber. Tube down from inhalation port down to bottom, "straw". There may be a patient interface incorporated into a separate part of the chamber other than the lid. For example, the aerosol is introduced through the lid, but inhalation is via a port or ports elsewhere in the body of the chamber.

It will be appreciated that inhaled vaccine provides for respiratory mucosal vaccination i.e. direct administration of a vaccine to the respiratory tract by either intranasal delivery or aerosol inhalation, can be beneficial particularly for diseases which utilise the respiratory tract as the initial site of infection e.g. SARS-CoV-2. A failure to accomplish early control of SARS-CoV-2 infection in the respiratory tract likely results in high viral burden and dysregulated, potentially lethal, inflammatory responses and immunopathology, including acute respiratory distress syndrome.

Research suggests that the respiratory mucosal route of vaccination is adept at inducing antibodies and lung tissue-resident memory T cells (TRM cells) in the respiratory mucosa, as well as macrophage-mediated trained immunity, which provide for an enhanced immunogenic response compared to other routes of vaccine administration.

As respiratory mucosal immunity is key to early clearance of severe acute respiratory syndrome coronavirus 2 (SARS- CoV-2), inducing trained immunity in alveolar macrophages and other innate cells through respiratory mucosal vaccination could be an effective strategy.

Respiratory mucosal vaccination also has the advantages of being needle-free and requiring a much smaller dose, possibly up to 80% less, than the parenteral route, allowing for immunization of considerably more people with the same starting volume of vaccine.

Advantageous Features of the Chamber and Apparatus A vibrating aperture plate is used for aerosolization and it has in excess of 2000 apertures per $mm^2$ and an ability to aerosolise a range of viscosities and surface tensions. The aerosolized liquid preferably has a viscosity in the range of 1 to 15 cP and a surface tension in the range of 0.5 mN/m and 72 mN/m, and it is preferred that the output rate is at least 0.01 mL/min. Potential agents to be delivered include, but are not limited to liposomes, exosomes, virus, RNA, DNA, phage, cells, non-viral vectors, antibodies, small molecular weight actives et cetera. These agents may or may not be loaded with a cargo such as genetic material (e.g., DNA/RNA) or active therapeutic/prophylactic.

The aperture plate preferably has a diameter more than 5 mm, for example 8 mm. It is preferred to have a large number of apertures and area in order to generate a target amount of aerosol per unit time without increasing driving voltage as one means of increasing output rate (and consequently increasing the temperature), the time to aerosolization of the full dose is minimised.

In some examples there may be two or more aerosol generators which supply aerosol to the chamber simultaneously. The advantage of this being the reduced time to aerosolization of the dose volume. It is preferred that the aperture plate has apertures with a diameter ranging from 1 to 6 microns. Apertures in this range minimise the heat and shear forces to which the agent is exposed to. It is preferred that the aerosol generator is deactivated at the end of a dose. The advantage here is this approach minimises the build-up of heat on the aerosol generator assembly that may adversely affect the agent being aerosolised.

The chamber may be configurable for attachment as appropriate to patient interfaces that facilitate lung (mouthpiece) or dual nose and lung targeting (facemask or nasal interface) of the aerosolised agent. The apparatus and/or chamber may be configured to be suitable for use with infant and paediatric patients. Children and infants are typically administered aerosol via a facemask, however, older children may be able to coordinate a breath through a mouthpiece.

TABLE

Typical Child and Infant Breathing Parameters

| Breath Parameters | Child | Infant |
|---|---|---|
| Tidal Volume | 155 ml | 50 ml |
| I:E Ratio | 1:2 | 1:3 |
| BPM | 25 | 30 |

TABLE

Summary of inhaled dose results for 330 ml chamber & 155 ml tidal volume (child breathing) via mouthpiece in lid - single breath.

| Chamber volume | Tidal Volume | Dose Volume (ml) | Delay Post Nebulisation (s) | Average % | STDEV |
|---|---|---|---|---|---|
| 330 ml | 155 ml | 0.1 | 1 | 8.02 | 0.44 |
| | | 0.1 | 5 | 6.57 | 0.17 |
| | | 0.1 | 10 | 5.99 | 0.17 |

The location from which the aerosol is inhaled is important with smaller patients. The combination of coordination of breathing and the ability to clear the chamber of aerosol with a low number of breaths is important. Here we present configurations that improve the inhaled dose significantly with use of a 330 mL chamber, and minimising the need for alterations to the dispensing station.

Alternative embodiments of chamber may be used, such as the following:
Configuration 1: Aerosol filled from the lid. Aerosol inhaled from close to the base of the chamber.
Configuration 2: Aerosol filled from the lid. Aerosol inhaled from middle of chamber.
Configuration 3: Aerosol filled from the lid. Aerosol inhaled from middle of chamber, with chamber orientated on the horizontal.
Configuration 4: Aerosol filled from the lid. Aerosol inhaled from the base of the chamber, with chamber orientated on the horizontal.

TABLE

Inhaled dose for Child breath settings with 330 ml chamber - multiple breaths.

| Chamber Configuration | Delay Post Nebulisation | Average % | STDEV |
|---|---|---|---|
| 1 | 1 Second | 27.17 | 1.13 |
| 1 | 5 Seconds | 24.40 | 0.79 |
| 1 | 10 Seconds | 22.26 | 0.38 |
| 1 | 30 Seconds | 15.97 | 1.70 |
| 2 | 1 Second | 33.21 | 0.75 |
| 2 | 5 Seconds | 27.80 | 0.79 |
| 2 | 10 Seconds | 24.15 | 1.00 |
| 2 | 30 Seconds | 17.99 | 0.44 |
| 3 | 1 Second | 21.76 | 2.08 |
| 3 | 5 Seconds | 16.73 | 1.15 |
| 3 | 10 Seconds | 15.60 | 0.58 |
| 3 | 30 Seconds | 13.58 | 0.38 |
| 4 | 1 Second | 24.78 | 0.79 |
| 4 | 5 Seconds | 17.61 | 0.79 |
| 4 | 10 Seconds | 13.08 | 0.95 |
| 4 | 30 Seconds | 10.19 | 0.75 |

TABLE

Inhaled dose for Infant breath settings with 330 ml chamber - multiple breaths.

| Chamber Option | Delay Post Nebulisation | Average % | Standard Deviation (STDEV) |
|---|---|---|---|
| 1 | 1 Second | 36.23 | 0.38 |
| 1 | 5 Seconds | 28.55 | 0.22 |
| 1 | 10 Seconds | 24.53 | 1.00 |
| 1 | 30 Seconds | 18.11 | 2.36 |
| 2 | 1 Second | 28.30 | 1.13 |
| 2 | 5 Seconds | 24.28 | 1.43 |

TABLE-continued

Inhaled dose for Infant breath settings with 330 ml chamber - multiple breaths.

| Chamber Option | Delay Post Nebulisation | Average % | Standard Deviation (STDEV) |
|---|---|---|---|
| 2 | 10 Seconds | 22.89 | 0.58 |
| 2 | 30 Seconds | 17.86 | 0.22 |
| 3 | 1 Second | 15.60 | 1.70 |
| 3 | 5 Seconds | 10.82 | 0.58 |
| 3 | 10 Seconds | 9.94 | 0.95 |
| 3 | 30 Seconds | 7.17 | 0.75 |
| 4 | 1 Second | 17.36 | 1.00 |
| 4 | 5 Seconds | 14.72 | 0.38 |
| 4 | 10 Seconds | 11.95 | 0.95 |
| 4 | 30 Seconds | 8.68 | 0.38 |

Given the smaller inhaled volumes from both child and infant, it may seem sensible to reduce the volume of the chamber in order to clear the smaller volume quicker. Results of testing below indicate that that is not the case. Here we assessed inhaled dose across four configurations/options and two chamber volumes (330 mL and 234 mL). This suggests that the 330 mL chamber is the optimal chamber volume across all patient types as a result of it minimising aerosol losses within the chamber post nebulisation, and before inhalation.

TABLE

Inhaled dose for Child breath settings with 234 ml chamber - multiple breaths.

| Chamber Option | Delay Post Nebulisation | Average % | STDEV |
|---|---|---|---|
| 1 | 1 Second | 26.54 | 0.44 |
| 1 | 5 Seconds | 24.03 | 0.79 |
| 1 | 10 Seconds | 22.01 | 1.21 |
| 1 | 30 Seconds | 15.22 | 1.53 |
| 2 | 1 Second | 28.30 | 0.38 |
| 2 | 5 Seconds | 24.78 | 1.53 |
| 2 | 10 Seconds | 19.37 | 1.33 |
| 2 | 30 Seconds | 15.85 | 0.38 |
| 3 | 1 Second | 20.63 | 1.86 |
| 3 | 5 Seconds | 17.86 | 0.95 |
| 3 | 10 Seconds | 13.21 | 3.72 |
| 3 | 30 Seconds | 7.04 | 0.44 |
| 4 | 1 Second | 22.64 | 2.10 |
| 4 | 5 Seconds | 13.33 | 0.22 |
| 4 | 10 Seconds | 9.69 | 0.79 |
| 4 | 30 Seconds | 6.92 | 0.79 |

TABLE

Inhaled dose for Infant breath settings with 234 ml chamber - multiple breaths.

| Chamber Option | Delay Post Nebulisation | Average % | STDEV |
|---|---|---|---|
| 1 | 1 Second | 26.42 | 0.38 |
| 1 | 5 Seconds | 24.78 | 1.78 |
| 1 | 10 Seconds | 22.77 | 0.58 |
| 1 | 30 Seconds | 15.09 | 1.36 |
| 2 | 1 Second | 23.90 | 1.33 |
| 2 | 5 Seconds | 20.75 | 0.38 |
| 2 | 10 Seconds | 19.37 | 0.44 |
| 2 | 30 Seconds | 15.47 | 0.65 |
| 3 | 1 Second | 15.60 | 2.31 |
| 3 | 5 Seconds | 12.45 | 0.65 |
| 3 | 10 Seconds | 9.94 | 1.21 |
| 3 | 30 Seconds | 5.66 | 0.38 |

TABLE-continued

Inhaled dose for Infant breath settings with 234 ml chamber - multiple breaths.

| Chamber Option | Delay Post Nebulisation | Average % | STDEV |
|---|---|---|---|
| 4 | 1 Second | 14.97 | 0.58 |
| 4 | 5 Seconds | 13.08 | 1.15 |
| 4 | 10 Seconds | 10.31 | 1.53 |
| 4 | 30 Seconds | 8.18 | 0.44 |

Configurations 3 and 4 above are intended to allow for filling of the chamber with aerosol, but orientated in such a fashion that it does not sit directly on front of the patient's eyes. Such an impact on the visual field may interfere with the patient's ability to follow instruction, and take focus away from the inhalation manoeuvre. However, these configurations were not seen to provide benefit from an inhaled dose performance. As such, a vertical, upright orientation for the chamber is preferred.

Another means of clearing the upright chamber of aerosol includes use of a tube inserted into the inner lumen of the chamber. That tube would be inserted into the hole into which the aerosol is introduced, after the aerosol generator was removed. The tube itself could be used as a mouthpiece, connected to a facemask or nasal interface for inhalation via the nose. The intent is to have the point of vacuum from the chamber (on inhalation) at a location at which maximal aerosol is entrained in the inhalation flow. This approach is appropriate for patients requiring a facemask for inhalation (adult, child and infant) Two configurations were assessed, from four (A, B, C, D) shown in FIG. 15:

Configuration A: Tube terminating approximately lcm from the base of the chamber.

Configuration B: Tube terminating approximately midway between base and top wall of chamber.

TABLE

| Tube in a 330 ml chamber (adult - single breath, child/infant - multiple breaths) | | | | |
|---|---|---|---|---|
| Parameters/ Chamber volume | Tube Position | Delay Post Nebulisation | Average % | STDEV |
| Adult (330 ml) | 1 cm from bottom | 1 Second | 24.78 | 5.34 |
| Adult (330 ml) | 1 cm from bottom | 5 Seconds | 23.14 | 1.90 |
| Adult (330 ml) | 1 cm from bottom | 10 Seconds | 22.52 | 1.94 |
| Adult (330 ml) | 1 cm from bottom | 30 Seconds | 14.21 | 2.46 |
| Adult (330 ml) | Halfway in chamber | 1 Second | 26.67 | 2.21 |
| Adult (330 ml) | Halfway in chamber | 5 Seconds | 27.04 | 1.33 |
| Adult (330 ml) | Halfway in chamber | 10 Seconds | 21.64 | 2.31 |
| Adult (330 ml) | Halfway in chamber | 30 Seconds | 14.72 | 1.00 |
| Child (330 ml) | 1 cm from bottom | 1 Second | 22.26 | 0.75 |
| Child (330 ml) | 1 cm from bottom | 5 Seconds | 22.39 | 0.79 |
| Child (330 ml) | 1 cm from bottom | 10 Seconds | 17.99 | 0.58 |
| Child (330 ml) | 1 cm from bottom | 30 Seconds | 5.91 | 0.44 |
| Child (330 ml) | Halfway in chamber | 1 Second | 22.89 | 0.44 |
| Child (330 ml) | Halfway in chamber | 5 Seconds | 22.52 | 0.44 |
| Child (330 ml) | Halfway in chamber | 10 Seconds | 20.13 | 1.57 |
| Child (330 ml) | Halfway in chamber | 30 Seconds | 7.42 | 0.58 |
| Infant (330 ml) | 1 cm from bottom | 1 Second | 14.84 | 0.22 |
| Infant (330 ml) | 1 cm from bottom | 5 Seconds | 14.84 | 0.58 |
| Infant (330 ml) | 1 cm from bottom | 10 Seconds | 12.20 | 0.58 |
| Infant (330 ml) | 1 cm from bottom | 30 Seconds | 5.41 | 1.21 |
| Infant (330 ml) | Halfway in chamber | 1 Second | 19.62 | 0.38 |
| Infant (330 ml) | Halfway in chamber | 5 Seconds | 19.37 | 0.58 |
| Infant (330 ml) | Halfway in chamber | 10 Seconds | 15.85 | 0.38 |
| Infant (330 ml) | Halfway in chamber | 30 Seconds | 5.91 | 0.22 |

TABLE

Tube in a 234 ml chamber with child and infant breath settings - multiple breaths

| Parameters/Chamber Size | Tube Position | Delay Post Nebulisation | Average % | STDEV |
|---|---|---|---|---|
| Child (234 ml) | 1 cm from bottom | 1 Second | 15.47 | 0.38 |
| Child (234 ml) | 1 cm from bottom | 5 Seconds | 15.72 | 0.22 |
| Child (234 ml) | 1 cm from bottom | 10 Seconds | 13.96 | 1.36 |
| Child (234 ml) | 1 cm from bottom | 30 Seconds | 4.40 | 0.58 |
| Child (234 ml) | Halfway in chamber | 1 Second | 21.01 | 0.79 |
| Child (234 ml) | Halfway in chamber | 5 Seconds | 20.88 | 0.22 |
| Child (234 ml) | Halfway in chamber | 10 Seconds | 16.73 | 1.15 |
| Child (234 ml) | Halfway in chamber | 30 Seconds | 9.06 | 1.31 |
| Infant (234 ml) | 1 cm from bottom | 1 Second | 13.21 | 0.65 |
| Infant (234 ml) | 1 cm from bottom | 5 Seconds | 13.21 | 0.38 |
| Infant (234 ml) | 1 cm from bottom | 10 Seconds | 11.19 | 0.22 |
| Infant (234 ml) | 1 cm from bottom | 30 Seconds | 4.78 | 0.079 |
| Infant (234 ml) | Halfway in chamber | 1 Second | 17.36 | 0.38 |
| Infant (234 ml) | Halfway in chamber | 5 Seconds | 17.36 | 0.38 |
| Infant (234 ml) | Halfway in chamber | 10 Seconds | 15.35 | 0.79 |
| Infant (234 ml) | Halfway in chamber | 30 Seconds | 8.43 | 0.95 |

It will be appreciated that the use of a vibrating mesh aperture plate aerosol generator helps to prevent shearing or the like damage to cells of microbiological medicaments such as vaccines. Such features are set out in our published PCT Specification No. WO2016/198667, the contents of which are incorporated herein by reference.

The invention is not limited to the embodiments described but may be varied in construction and detail. The dispensing nebulizer is preferably of the vibrating aperture plate type, and a jet nebuliser would be less suitable, as the driving gas might clear the chamber. In general, it is preferred that the nebulizer be of the type having vibrating mesh aerosol generators, or a surface acoustic wave, or a Fourier horn type aerosol generator.

In various preferred embodiments the aerosol dispenser detects the chamber is in its correct position and delivers a pre-determined dose of aerosol. Once the dose is delivered a visual and/or audible indicator informs the user that the chamber is filled and that they can take the inhalation. This is a very beneficial part of operation of the user interface 103.

The top wall with the aerosol inlet may be slanted, and/or the nebulizer outlet conduit may be slanted for delivery towards or away from the side wall according to desired filling effects. Also, there may be an additional opening in the top wall, such as slit near the edge, to assist flow during inhalation.

The dispensing stage may have any suitable support for a chamber being filled. In one example it is simply a platform for the chamber to rest on, and in another it comprises a receiver ring on a rotating arm. It may however in other examples comprise a gripping mechanism to positively grip the chamber by for example opposed jaws. Where the chamber is gripped in some way, it may in some examples be turned and orientated for optimum delivery. Also, the dispensing apparatus may be adapted to dispense aerosol other than vaccines, such as monoclonal antibodies or other treatments. Also, the chamber may have a baffle near the aerosol inlet, to provide selective rain-out for filtering the droplet sizes. In this way a chamber may be suited to a particular type of aerosol to optimize effectiveness. The baffle may for example take the form of a tube extending inwardly from the aerosol inlet.

Any feature described for one embodiment may be employed to perform an equivalent function in an apparatus or chamber of a different embodiment as would be understood by those skilled in the art.

The invention claimed is:

1. An aerosol dispensing apparatus comprising a controller, a dispenser with a support for a single dose aerosol chamber having a nebulizer delivery port and an inhalation port, and a nebulizer having an aerosol generator and an outlet conduit adapted to deliver an aerosol dose into the single dose aerosol chamber via the nebulizer delivery port, wherein the dispenser is configured for automatic engagement of the nebulizer outlet conduit with the nebulizer delivery port and for separation after delivery of a dose.

2. The apparatus of claim 1, wherein the dispenser comprises an automated chamber handler for engagement of the single dose aerosol chamber with the nebulizer in an automated manner.

3. The apparatus of claim 1, wherein the nebulizer is configured to deliver doses according to a pre-set time at a pre-set flow rate.

4. The apparatus of claim 1, further comprising a chamber dispenser for dispensing the single dose aerosol chamber to a user in proximity to the nebulizer.

5. The apparatus of claim 1, further comprising a user interface with a display screen and/or a speaker, and the controller is configured to generate user instructions for use of the apparatus and for inhalation from the single dose aerosol chamber.

6. The apparatus of claim 5, wherein the controller is configured to instruct user inhalation from the single dose aerosol chamber within a set period of time.

7. The apparatus of claim 5, wherein the controller is configured to provide instructions to consume the aerosol within 10 seconds.

8. The apparatus of claim 5, wherein the controller is configured to generate an advisory communication via the interface concerning a desired number of inhalations and breaths.

9. The apparatus of claim 8, wherein the controller is configured to generate an advisory communication advising a maximum of two breaths.

10. The apparatus of claim 8, wherein the controller is configured to generate an advisory communication to advise a user to have a short inhalation.

11. The apparatus of claim 1, further comprising a receptacle for receiving the single dose aerosol chamber after the single dose aerosol chamber after the single dose aerosol chamber has been dispensed from the apparatus.

12. The apparatus of claim 1, wherein the apparatus is arranged in a series of stages including a stage for (a) dispensing the single dose aerosol chamber, (b) for filling the single dose aerosol chamber, and (c) for disposing of the single dose aerosol chamber.

13. The apparatus of claim 1, wherein the nebulizer is configured to deliver doses of between 0.05 mL and 0.25 mL.

14. The apparatus of claim 1, wherein the nebulizer is configured to deliver at a flow rate in excess of 0.01 mL/min.

15. The apparatus of claim 14, wherein the nebulizer is configured to deliver at a flow rate in the range of 0.5 mL/min to 2.5 mL/min.

16. The apparatus of claim 1, wherein the nebulizer is configured for delivery of aerosol into the single dose aerosol chamber in less than 15 seconds.

17. The apparatus of claim 1, wherein the dispenser comprises an automated chamber handler for engagement of the single dose aerosol chamber with the nebulizer in an automated manner, and said handler comprises a chamber holder which is movable from a chamber receiving position to an aerosol generator engagement position.

18. The apparatus of claim 17, wherein the automated chamber handler comprises a sensor configured to detect a presence of the single dose aerosol chamber in the automated chamber handler, and the controller is configured to trigger a filling cycle upon detection of the presence of the single dose aerosol chamber in the automated chamber handler.

19. The apparatus of claim 18, wherein the sensor is further configured to detect concentricity of the single dose aerosol chamber in the automated chamber handler.

20. The apparatus of claim 18, wherein the automated chamber handler is on an arm which is rotatable from a chamber-receiving and user-facing front position to a filling rear position.

21. The apparatus of claim 20, wherein the arm supports a dispensing stage cover at an end opposed from the automated chamber handler, such that the dispensing stage cover is presented to a user during filling of the single dose aerosol chamber to provide an interlock.

22. The apparatus of claim 21, wherein the dispensing stage cover is curved to present a convex surface towards a front of the apparatus.

23. The apparatus of claim 1, wherein the nebulizer comprises a nebulizer support which supports the aerosol generator during movement from an inoperative position to an operative position for filling of the single dose aerosol chamber.

24. The apparatus of claim 23, wherein the inoperative position is above the single dose aerosol chamber.

25. The apparatus of claim 23, wherein the nebulizer support is movable on a vertical rail to move the aerosol generator between the inoperative position and the operative position.

26. The apparatus of claim 1, wherein the nebulizer comprises a chamber sensor configured to detect a presence of the single dose aerosol chamber in engagement with the outlet conduit, and the controller is configured to commence aerosolization only upon said detection of the presence of the single dose aerosol chamber.

27. The apparatus of claim 1, wherein the nebulizer comprises a pusher to push against the single dose aerosol chamber during disengagement of the outlet conduit to prevent movement of the single dose aerosol chamber or a lid of the single dose aerosol chamber.

28. The apparatus of claim 1, wherein the nebulizer comprises:

a vibratory mesh aperture plate having an upper reservoir layer with liquid supply cavities including a diameter in the range of 20 µm to 400 µm and a lower layer of aerosol-forming apertures, wherein the aperture plate includes in excess of 100 aerosol-forming apertures per square mm, the aerosol-forming apertures being sized to provide aerosol droplets, and at least 80% of the aerosol-forming apertures have a size less than 6 µm;

a vibration drive for causing vibration of the aperture plate; and a reservoir for delivering a treatment liquid to a top surface of the aperture plate, such that vibration of the aperture plate causes aerosol to enter the outlet conduit.

29. The apparatus of claim 28, wherein the nebulizer is configured to automatically detect end of dose on the aperture plate and to stop operation of the nebulizer if there is no liquid on the aperture plate and provide an alert at a user interface accordingly.

30. The apparatus of claim 29, wherein the controller is configured to perform steps of:

measuring aperture plate drive current at each of a plurality of measuring points in a scan, each measuring point having a drive frequency, wherein the controller is configured to perform the scan across a drive frequency range of 128 kHz to 165 kHz;

determining a minimum value of the drive current in said scan;

determining a value for maximum rate of change of drive current during the scan; and using the minimum value in combination with said maximum rate of change value to execute an algorithm to calculate an indicator value for end-of-dose, wherein the controller is configured to utilize a ratio of a maximum slope value and a minimum parameter value to calculate said indicator.

31. The apparatus of claim 1, wherein the nebulizer is configured to supply only a single dose to the aerosol generator for the dispensing operation of filling the single dose aerosol chamber.

32. A method of providing aerosol for treating a patient with the apparatus of claim 1, the method comprising:

automatically delivering an aerosol dose into the single dose aerosol chamber; and automatically providing instructions via a user interface to a user for inhalation.

* * * * *